United States Patent
Shalev

(10) Patent No.: US 9,770,350 B2
(45) Date of Patent: Sep. 26, 2017

(54) STENT-GRAFT WITH FIXATION ELEMENTS THAT ARE RADIALLY CONFINED FOR DELIVERY

(75) Inventor: Alon Shalev, Ra'anana (IL)

(73) Assignee: ENDOSPAN LTD., Herzilyia Pituah (IL)

( * ) Notice: Subject to any disclaimer, the term of this patent is extended or adjusted under 35 U.S.C. 154(b) by 179 days.

(21) Appl. No.: 14/400,699

(22) PCT Filed: May 15, 2012

(86) PCT No.: PCT/IL2012/000190
§ 371 (c)(1),
(2), (4) Date: Jan. 6, 2015

(87) PCT Pub. No.: WO2013/171730
PCT Pub. Date: Nov. 21, 2013

(65) Prior Publication Data
US 2015/0142096 A1   May 21, 2015

(51) Int. Cl.
*A61F 2/06*   (2013.01)
*A61F 2/95*   (2013.01)
(Continued)

(52) U.S. Cl.
CPC ............ *A61F 2/95* (2013.01); *A61F 2/07* (2013.01); *A61F 2/82* (2013.01); *A61F 2/966* (2013.01);
(Continued)

(58) Field of Classification Search
CPC .... A61F 2/07; A61F 2/95; A61F 2/966; A61F 2/84; A61F 2002/075; A61F 2002/8483
See application file for complete search history.

(56) References Cited

U.S. PATENT DOCUMENTS

| 4,180,613 A | 12/1979 | Vassiliou |
| 4,355,426 A | 10/1982 | MacGregor |

(Continued)

FOREIGN PATENT DOCUMENTS

| CA | 2497704 | 3/2004 |
| CN | 2453960 | 10/2001 |

(Continued)

OTHER PUBLICATIONS

European search report issued in Application No. 10832752.9, dated May 23, 2016.
(Continued)

*Primary Examiner* — Victor Nguyen
(74) *Attorney, Agent, or Firm* — Sughrue Mion, PLLC

(57) ABSTRACT

An endovascular stent-graft is provided that includes a flexible stent member, which includes a plurality of struts, which are shaped so as to define a generally circumferential section; a tubular fluid flow guide, which includes a graft material, and which is attached to the stent member; and at least one fixation member shaped so as to define a base at a first end thereof and a sharp tip at a second end thereof. The base is coupled to one of the struts that are shaped so as to define the generally circumferential section. When the stent-graft is in a radially-expanded deployment state, the fixation member protrudes radially outward. When the stent-graft is in a radially-compressed delivery state, at least a portion of the fixation member between the base and the sharp tip is convex as viewed from outside the stent-graft, such that the sharp tip points radially inward.

15 Claims, 8 Drawing Sheets

(51) Int. Cl.
*A61F 2/07* (2013.01)
*A61F 2/82* (2013.01)
*A61F 2/966* (2013.01)
*A61F 2/848* (2013.01)

(52) U.S. Cl.
CPC . *A61F 2002/075* (2013.01); *A61F 2002/8483* (2013.01)

(56) References Cited

U.S. PATENT DOCUMENTS

| | | |
|---|---|---|
| 4,505,767 A | 3/1985 | Quin |
| 4,562,596 A | 1/1986 | Kornberg |
| 4,577,631 A | 3/1986 | Kreamer |
| 4,617,932 A | 10/1986 | Kornberg |
| 4,665,906 A | 5/1987 | Jervis |
| 4,739,762 A | 4/1988 | Palmaz |
| 4,787,899 A | 11/1988 | Lazarus |
| 4,878,906 A | 11/1989 | Lindemann et al. |
| 4,886,062 A | 12/1989 | Wiktor |
| 4,938,740 A | 7/1990 | Melbin |
| 4,969,458 A | 11/1990 | Wiktor |
| 5,042,707 A | 8/1991 | Taheri |
| 5,064,435 A | 11/1991 | Porter |
| 5,104,404 A | 4/1992 | Wolff |
| 5,122,136 A | 6/1992 | Guglielmi et al. |
| 5,129,910 A | 7/1992 | Phan et al. |
| 5,133,732 A | 7/1992 | Wiktor |
| 5,192,256 A | 3/1993 | Ryan |
| 5,192,286 A | 3/1993 | Phan et al. |
| 5,234,448 A | 8/1993 | Wholey et al. |
| 5,383,926 A | 1/1995 | Lock et al. |
| 5,456,694 A | 10/1995 | Marin et al. |
| 5,486,183 A | 1/1996 | Middleman et al. |
| 5,507,769 A | 4/1996 | Marin et al. |
| 5,509,923 A | 4/1996 | Middleman et al. |
| 5,522,880 A | 6/1996 | Barone et al. |
| 5,527,322 A | 6/1996 | Klein et al. |
| 5,549,662 A | 8/1996 | Fordenbacher |
| 5,554,181 A | 9/1996 | Das |
| 5,556,413 A | 9/1996 | Lam |
| 5,562,724 A | 10/1996 | Vorwerk et al. |
| 5,607,445 A | 3/1997 | Summers |
| 5,613,974 A | 3/1997 | Andreas et al. |
| 5,632,746 A | 5/1997 | Middleman et al. |
| 5,632,763 A | 5/1997 | Glastra |
| 5,632,772 A | 5/1997 | Alcime et al. |
| 5,639,278 A | 6/1997 | Dereume et al. |
| 5,643,340 A | 7/1997 | Nunokawa |
| 5,653,743 A | 8/1997 | Martin |
| 5,676,696 A | 10/1997 | Marcade |
| 5,676,697 A | 10/1997 | McDonald |
| 5,693,084 A | 12/1997 | Chuter |
| 5,728,134 A | 3/1998 | Barak |
| 5,749,879 A | 5/1998 | Middleman et al. |
| 5,755,770 A | 5/1998 | Ravenscroft |
| 5,755,771 A | 5/1998 | Penn et al. |
| 5,755,777 A | 5/1998 | Chuter |
| 5,755,781 A | 5/1998 | Jayaraman |
| 5,769,882 A | 6/1998 | Fogarty et al. |
| 5,769,884 A | 6/1998 | Solovay |
| 5,782,903 A | 7/1998 | Wiktor |
| 5,782,906 A | 7/1998 | Marshall et al. |
| 5,824,040 A | 10/1998 | Cox et al. |
| 5,824,055 A | 10/1998 | Spiridigliozzi et al. |
| 5,827,321 A | 10/1998 | Roubin et al. |
| 5,843,170 A | 12/1998 | Ahn |
| 5,855,600 A | 1/1999 | Alt |
| 5,860,991 A | 1/1999 | Klein et al. |
| 5,876,432 A | 3/1999 | Lau et al. |
| 5,906,641 A | 5/1999 | Thompson et al. |
| 5,921,994 A | 7/1999 | Andreas et al. |
| 5,925,076 A | 7/1999 | Inoue |
| 5,948,018 A | 9/1999 | Dereume et al. |
| 5,968,091 A | 10/1999 | Pinchuk et al. |
| 5,980,552 A | 11/1999 | Pinchasik et al. |
| 5,984,955 A | 11/1999 | Wisselink |
| 6,015,431 A | 1/2000 | Thornton et al. |
| 6,016,810 A | 1/2000 | Ravenscroft |
| 6,030,414 A | 2/2000 | Taheri |
| 6,033,435 A | 3/2000 | Penn et al. |
| 6,036,723 A | 3/2000 | Anidjar et al. |
| 6,036,725 A | 3/2000 | Avellanet |
| 6,049,824 A | 4/2000 | Simonin |
| 6,051,021 A | 4/2000 | Frid |
| 6,059,824 A | 5/2000 | Taheri |
| 6,099,497 A | 8/2000 | Adams et al. |
| 6,099,548 A | 8/2000 | Taheri |
| 6,117,145 A | 9/2000 | Wood et al. |
| 6,129,738 A | 10/2000 | Lashinski et al. |
| 6,132,457 A | 10/2000 | Chobotov |
| 6,156,064 A | 12/2000 | Chouinard |
| 6,159,228 A | 12/2000 | Frid et al. |
| 6,176,875 B1 | 1/2001 | Lenker et al. |
| 6,179,878 B1 | 1/2001 | Duerig et al. |
| 6,200,339 B1 | 3/2001 | Leschinsky et al. |
| 6,206,893 B1 | 3/2001 | Klein et al. |
| 6,270,524 B1 | 8/2001 | Kim |
| 6,283,991 B1 | 9/2001 | Cox et al. |
| 6,287,335 B1 | 9/2001 | Drasler et al. |
| 6,290,720 B1 | 9/2001 | Khosravi et al. |
| 6,296,661 B1 | 10/2001 | Davila et al. |
| 6,312,458 B1 | 11/2001 | Golds |
| 6,325,819 B1 | 12/2001 | Pavcnik et al. |
| 6,325,823 B1 | 12/2001 | Horzewski et al. |
| 6,344,056 B1 | 2/2002 | Dehdashtian |
| 6,395,018 B1 | 5/2002 | Castaneda |
| 6,406,420 B1 | 6/2002 | McCarthy et al. |
| 6,428,565 B1 | 8/2002 | Wisselink |
| 6,451,051 B2 | 9/2002 | Drasler et al. |
| 6,471,722 B1 | 10/2002 | Inoue |
| 6,506,211 B1 | 1/2003 | Skubitz et al. |
| 6,520,988 B1 | 2/2003 | Colombo et al. |
| 6,544,279 B1 | 4/2003 | Hopkins et al. |
| 6,565,597 B1 | 5/2003 | Fearnot et al. |
| 6,576,009 B2 | 6/2003 | Ryan et al. |
| 6,613,078 B1 | 9/2003 | Barone |
| 6,635,083 B1 | 10/2003 | Cheng et al. |
| 6,645,242 B1 | 11/2003 | Quinn |
| 6,648,911 B1 | 11/2003 | Sirhan et al. |
| 6,652,567 B1 | 11/2003 | Deaton |
| 6,652,571 B1 | 11/2003 | White et al. |
| 6,656,214 B1 | 12/2003 | Fogarty et al. |
| 6,673,080 B2 | 1/2004 | Reynolds et al. |
| 6,692,520 B1 | 2/2004 | Gambale et al. |
| 6,695,833 B1 | 2/2004 | Frantzen |
| 6,695,875 B2 | 2/2004 | Stelter et al. |
| 6,699,277 B1 | 3/2004 | Freidberg et al. |
| 6,716,238 B2 | 4/2004 | Elliott |
| 6,729,356 B1 | 5/2004 | Baker et al. |
| 6,733,523 B2 | 5/2004 | Shaolian et al. |
| 6,743,195 B2 | 6/2004 | Zucker |
| 6,752,826 B2 | 6/2004 | Holloway et al. |
| 6,776,794 B1 | 8/2004 | Hong et al. |
| 6,808,534 B1 | 10/2004 | Escano |
| 6,814,749 B2 | 11/2004 | Cox et al. |
| 6,814,752 B1 | 11/2004 | Chuter |
| 6,824,560 B2 | 11/2004 | Pelton |
| 6,843,803 B2 | 1/2005 | Ryan et al. |
| 6,846,321 B2 | 1/2005 | Zucker |
| 6,860,900 B2 | 3/2005 | Clerc et al. |
| 6,907,285 B2 | 6/2005 | Denker et al. |
| 6,908,477 B2 | 6/2005 | McGuckin, Jr. et al. |
| 6,929,660 B1 | 8/2005 | Ainsworth et al. |
| 6,942,691 B1 | 9/2005 | Chuter |
| 6,964,679 B1 | 11/2005 | Marcade et al. |
| 6,986,774 B2 | 1/2006 | Middleman et al. |
| 7,008,441 B2 | 3/2006 | Zucker |
| 7,018,400 B2 | 3/2006 | Lashinski et al. |
| 7,022,131 B1 | 4/2006 | Derowe et al. |
| 7,044,962 B2 | 5/2006 | Elliott |
| 7,105,015 B2 | 9/2006 | Goshgarian |
| 7,105,020 B2 | 9/2006 | Greenberg et al. |
| 7,112,217 B1 | 9/2006 | Kugler et al. |

(56) References Cited

U.S. PATENT DOCUMENTS

| | | |
|---|---|---|
| 7,115,127 B2 | 10/2006 | Lindenbaum et al. |
| 7,122,052 B2 | 10/2006 | Greenhalgh |
| 7,131,991 B2 | 11/2006 | Zarins et al. |
| 7,144,421 B2 | 12/2006 | Carpenter et al. |
| 7,160,318 B2 | 1/2007 | Greenberg et al. |
| 7,175,651 B2 | 2/2007 | Kerr |
| 7,198,638 B2 | 4/2007 | Dong |
| 7,201,772 B2 | 4/2007 | Schwammenthal et al. |
| 7,220,274 B1 | 5/2007 | Quinn |
| 7,223,266 B2 | 5/2007 | Lindenbaum et al. |
| 7,270,675 B2 | 9/2007 | Chun et al. |
| 7,279,003 B2 | 10/2007 | Berra et al. |
| 7,294,145 B2 | 11/2007 | Ward |
| 7,294,147 B2 | 11/2007 | Hartley |
| 7,306,623 B2 | 12/2007 | Watson |
| 7,341,598 B2 | 3/2008 | Davidson et al. |
| 7,393,357 B2 | 7/2008 | Stelter et al. |
| 7,396,363 B2 | 7/2008 | Frid |
| 7,407,509 B2 | 8/2008 | Greenberg et al. |
| 7,413,573 B2 | 8/2008 | Hartley et al. |
| 7,425,219 B2 | 9/2008 | Quadri |
| 7,429,269 B2 | 9/2008 | Schwammenthal et al. |
| 7,438,721 B2 | 10/2008 | Doig et al. |
| 7,442,204 B2 | 10/2008 | Schwammenthal et al. |
| 7,473,272 B2 | 1/2009 | Pryor |
| 7,491,231 B2 | 2/2009 | Nazzaro et al. |
| 7,537,606 B2 | 5/2009 | Hartley et al. |
| 7,537,609 B2 | 5/2009 | Davidson et al. |
| 7,540,881 B2 | 6/2009 | Meyer et al. |
| 7,544,160 B2 | 6/2009 | Gross |
| 7,575,590 B2 | 8/2009 | Watson |
| 7,637,939 B2 | 12/2009 | Tischler |
| 7,645,298 B2 | 1/2010 | Hartley et al. |
| 7,655,036 B2 | 2/2010 | Goodson |
| 7,655,037 B2 | 2/2010 | Fleming, III et al. |
| 7,662,161 B2 | 2/2010 | Briganti et al. |
| 7,662,168 B2 | 2/2010 | McGuckin, Jr. et al. |
| 7,670,369 B2 | 3/2010 | Schaeffer |
| 7,678,141 B2 | 3/2010 | Greenan et al. |
| 7,699,885 B2 | 4/2010 | Leonhardt et al. |
| 7,708,704 B2 | 5/2010 | Mitelberg et al. |
| 7,722,626 B2 | 5/2010 | Middleman et al. |
| 7,731,732 B2 | 6/2010 | Ken |
| 7,766,955 B2 | 8/2010 | Vardi et al. |
| 7,771,465 B2 | 8/2010 | Zukowski |
| 7,789,903 B2 | 9/2010 | Spiridigliozzi et al. |
| 7,803,178 B2 | 9/2010 | Whirley et al. |
| 7,806,923 B2 | 10/2010 | Moloney |
| 7,815,673 B2 | 10/2010 | Bloom et al. |
| 7,833,259 B2 | 11/2010 | Boatman |
| 7,846,194 B2 | 12/2010 | Hartley et al. |
| 7,850,725 B2 | 12/2010 | Vardi et al. |
| 7,867,270 B2 | 1/2011 | Hartley et al. |
| 7,887,575 B2 | 2/2011 | Kujawski |
| 7,914,572 B2 | 3/2011 | Hartley et al. |
| 7,914,574 B2 | 3/2011 | Schmid et al. |
| 7,955,373 B2 | 6/2011 | Sowinski et al. |
| 7,955,374 B2 | 6/2011 | Erickson et al. |
| 7,959,662 B2 | 6/2011 | Erbel et al. |
| 7,959,669 B2 | 6/2011 | Chalekian et al. |
| 7,998,186 B2 | 8/2011 | Hartley |
| 7,998,187 B2 | 8/2011 | Hartley et al. |
| 8,012,193 B2 | 9/2011 | Hartley et al. |
| 8,021,412 B2 | 9/2011 | Hartley et al. |
| 8,021,418 B2 | 9/2011 | Gerberding et al. |
| 8,021,419 B2 | 9/2011 | Hartley et al. |
| 8,043,365 B2 | 10/2011 | Thramann |
| 8,048,139 B2 | 11/2011 | Frid et al. |
| 8,048,140 B2 | 11/2011 | Purdy |
| 8,048,147 B2 | 11/2011 | Adams |
| 8,052,736 B2 | 11/2011 | Doig et al. |
| 8,052,741 B2 | 11/2011 | Bruszewski et al. |
| 8,066,755 B2 | 11/2011 | Zacharias et al. |
| 8,080,053 B2 | 12/2011 | Satasiya et al. |
| 8,100,960 B2 | 1/2012 | Bruszewski |
| 8,118,854 B2 | 2/2012 | Bowe |
| 8,133,267 B2 | 3/2012 | Leonhardt et al. |
| 8,157,810 B2 | 4/2012 | Case et al. |
| 8,167,926 B2 | 5/2012 | Hartley et al. |
| 8,172,892 B2 | 5/2012 | Chuter et al. |
| 8,172,895 B2 | 5/2012 | Anderson et al. |
| 8,197,475 B2 | 6/2012 | Bruszewski et al. |
| 8,197,533 B2 | 6/2012 | Kujawski |
| 8,211,158 B2 | 7/2012 | Wolf |
| 8,216,298 B2 | 7/2012 | Wright et al. |
| 8,221,494 B2 | 7/2012 | Schreck et al. |
| 8,226,706 B2 | 7/2012 | Hartley et al. |
| 8,236,040 B2 | 8/2012 | Mayberry et al. |
| 8,251,963 B2 | 8/2012 | Chin et al. |
| 8,257,423 B2 | 9/2012 | Kerr |
| 8,262,719 B2 | 9/2012 | Erickson et al. |
| 8,273,115 B2 | 9/2012 | Hamer et al. |
| 8,287,586 B2 | 10/2012 | Schaeffer et al. |
| 8,292,885 B2 | 10/2012 | Bruszewski et al. |
| 8,292,941 B2 | 10/2012 | Muzslay |
| 8,292,949 B2 | 10/2012 | Berra et al. |
| 8,292,951 B2 | 10/2012 | Muzslay |
| 8,333,800 B2 | 12/2012 | Bruszewski et al. |
| 8,337,546 B2 | 12/2012 | Bruszewski |
| 8,353,898 B2 | 1/2013 | Lutze et al. |
| 8,357,192 B2 | 1/2013 | Mayberry et al. |
| 8,361,134 B2 | 1/2013 | Hartley et al. |
| 8,394,136 B2 | 3/2013 | Hartley et al. |
| 8,425,585 B2 | 4/2013 | Melsheimer et al. |
| 8,470,018 B2 | 6/2013 | Hartley et al. |
| 8,475,513 B2 | 7/2013 | Sithian |
| 8,480,726 B2 | 7/2013 | Cunningham et al. |
| 8,486,131 B2 | 7/2013 | Shalev |
| 8,491,646 B2 | 7/2013 | Schreck |
| 8,506,622 B2 | 8/2013 | Bruszewski et al. |
| 8,870,938 B2 | 10/2014 | Shalev et al. |
| 8,968,384 B2 | 3/2015 | Pearson et al. |
| 9,168,123 B2 | 10/2015 | Barrand |
| 2001/0000188 A1 | 4/2001 | Lenker et al. |
| 2001/0004705 A1 | 6/2001 | Killion et al. |
| 2001/0014823 A1 | 8/2001 | Ressemann et al. |
| 2001/0034550 A1 | 10/2001 | Buirge et al. |
| 2001/0037142 A1 | 11/2001 | Stelter et al. |
| 2001/0044647 A1 | 11/2001 | Pinchuk et al. |
| 2001/0044651 A1 | 11/2001 | Steinke et al. |
| 2001/0044652 A1 | 11/2001 | Moore |
| 2001/0047198 A1 | 11/2001 | Drasler et al. |
| 2001/0049550 A1 | 12/2001 | Martin et al. |
| 2001/0053930 A1 | 12/2001 | Kugler et al. |
| 2002/0040236 A1 | 4/2002 | Lau et al. |
| 2002/0052643 A1 | 5/2002 | Wholey et al. |
| 2002/0052644 A1 | 5/2002 | Shaolian et al. |
| 2002/0072790 A1 | 6/2002 | McGuckin, Jr. et al. |
| 2002/0099438 A1 | 7/2002 | Furst |
| 2002/0099441 A1 | 7/2002 | Dehdashtian |
| 2002/0107564 A1 | 8/2002 | Cox et al. |
| 2002/0111667 A1 | 8/2002 | Girton et al. |
| 2002/0123791 A1 | 9/2002 | Harrison |
| 2002/0156495 A1 | 10/2002 | Brenneman et al. |
| 2002/0156517 A1 | 10/2002 | Perouse |
| 2002/0173809 A1 | 11/2002 | Fleischman et al. |
| 2002/0183783 A1 | 12/2002 | Shadduck |
| 2002/0193864 A1 | 12/2002 | Khosravi et al. |
| 2002/0198585 A1 | 12/2002 | Wisselink |
| 2003/0033005 A1 | 2/2003 | Houser et al. |
| 2003/0040791 A1 | 2/2003 | Oktay |
| 2003/0065345 A1* | 4/2003 | Weadock ......... A61B 17/06166 606/153 |
| 2003/0065386 A1 | 4/2003 | Weadock |
| 2003/0068296 A1 | 4/2003 | Ricci et al. |
| 2003/0074055 A1 | 4/2003 | Haverkost |
| 2003/0093145 A1 | 5/2003 | Lawrence-Brown et al. |
| 2003/0125796 A1 | 7/2003 | Dong |
| 2003/0130720 A1 | 7/2003 | DePalma et al. |
| 2003/0144725 A1 | 7/2003 | Lombardi |
| 2003/0153944 A1 | 8/2003 | Phung et al. |
| 2003/0153968 A1 | 8/2003 | Geis et al. |
| 2003/0171771 A1 | 9/2003 | Anderson et al. |
| 2003/0191523 A1 | 10/2003 | Hojeibane |

(56) References Cited

U.S. PATENT DOCUMENTS

| | | |
|---|---|---|
| 2003/0199967 A1 | 10/2003 | Hartley et al. |
| 2003/0199968 A1 | 10/2003 | Ainsworth et al. |
| 2003/0204236 A1 | 10/2003 | Letort |
| 2003/0204242 A1 | 10/2003 | Zarins et al. |
| 2003/0204243 A1 | 10/2003 | Shiu |
| 2003/0212449 A1 | 11/2003 | Cox |
| 2003/0233117 A1 | 12/2003 | Adams et al. |
| 2003/0236567 A1 | 12/2003 | Elliot |
| 2004/0015227 A1 | 1/2004 | Vardi et al. |
| 2004/0015229 A1 | 1/2004 | Fulkerson et al. |
| 2004/0098091 A1 | 5/2004 | Erbel et al. |
| 2004/0106972 A1 | 6/2004 | Deaton |
| 2004/0106978 A1 | 6/2004 | Greenberg et al. |
| 2004/0117003 A1 | 6/2004 | Ouriel et al. |
| 2004/0133266 A1 | 7/2004 | Clerc et al. |
| 2004/0138735 A1 | 7/2004 | Shaolian et al. |
| 2004/0162606 A1 | 8/2004 | Thompson |
| 2004/0171978 A1 | 9/2004 | Shalaby |
| 2004/0181149 A1 | 9/2004 | Langlotz et al. |
| 2004/0215319 A1 | 10/2004 | Berra et al. |
| 2004/0215327 A1 | 10/2004 | Doig et al. |
| 2004/0215332 A1 | 10/2004 | Frid |
| 2004/0260383 A1 | 12/2004 | Stelter et al. |
| 2005/0010246 A1 | 1/2005 | Streeter et al. |
| 2005/0033406 A1 | 2/2005 | Barnhart et al. |
| 2005/0049678 A1 | 3/2005 | Cocks et al. |
| 2005/0065545 A1 | 3/2005 | Wallace |
| 2005/0085900 A1 | 4/2005 | Case et al. |
| 2005/0102018 A1 | 5/2005 | Carpenter et al. |
| 2005/0102021 A1 | 5/2005 | Osborne |
| 2005/0131517 A1 | 6/2005 | Hartley et al. |
| 2005/0137682 A1 | 6/2005 | Justino |
| 2005/0149166 A1 | 7/2005 | Schaeffer et al. |
| 2005/0154448 A1 | 7/2005 | Cully et al. |
| 2005/0159803 A1 | 7/2005 | Lad et al. |
| 2005/0165480 A1 | 7/2005 | Jordan et al. |
| 2005/0171598 A1 | 8/2005 | Schaeffer |
| 2005/0171599 A1 | 8/2005 | White |
| 2005/0177132 A1 | 8/2005 | Lentz et al. |
| 2005/0177224 A1 | 8/2005 | Fogarty et al. |
| 2005/0203606 A1 | 9/2005 | VanCamp |
| 2005/0216018 A1 | 9/2005 | Sennett |
| 2005/0222667 A1 | 10/2005 | Hunt |
| 2005/0222668 A1 | 10/2005 | Schaeffer et al. |
| 2005/0222669 A1 | 10/2005 | Purdy |
| 2005/0228480 A1 | 10/2005 | Douglas et al. |
| 2005/0234542 A1 | 10/2005 | Melsheimer |
| 2005/0266042 A1 | 12/2005 | Tseng |
| 2005/0273155 A1 | 12/2005 | Bahler et al. |
| 2005/0283188 A1 | 12/2005 | Loshakove et al. |
| 2006/0015170 A1 | 1/2006 | Jones et al. |
| 2006/0030921 A1 | 2/2006 | Chu |
| 2006/0052799 A1 | 3/2006 | Middleman et al. |
| 2006/0069426 A1 | 3/2006 | Weinberger |
| 2006/0095114 A1 | 5/2006 | Hartley et al. |
| 2006/0100684 A1 | 5/2006 | Elliott |
| 2006/0106406 A1 | 5/2006 | Weinberger |
| 2006/0116748 A1 | 6/2006 | Kaplan et al. |
| 2006/0149360 A1 | 7/2006 | Schwammenthal et al. |
| 2006/0155358 A1 | 7/2006 | LaDuca et al. |
| 2006/0155359 A1 | 7/2006 | Watson |
| 2006/0155366 A1 | 7/2006 | LaDuca et al. |
| 2006/0167476 A1 | 7/2006 | Burdulis et al. |
| 2006/0173530 A1 | 8/2006 | Das |
| 2006/0178733 A1* | 8/2006 | Pinchuk .................. A61F 2/07 623/1.35 |
| 2006/0190070 A1 | 8/2006 | Dieck et al. |
| 2006/0193892 A1 | 8/2006 | Furst et al. |
| 2006/0229709 A1 | 10/2006 | Morris et al. |
| 2006/0241740 A1 | 10/2006 | Vardi et al. |
| 2006/0271166 A1 | 11/2006 | Thill et al. |
| 2006/0276882 A1 | 12/2006 | Case et al. |
| 2006/0281966 A1 | 12/2006 | Peacock, III |
| 2006/1010640 | 12/2006 | Peacock, III |
| 2007/0016281 A1 | 1/2007 | Melsheimer |
| 2007/0021822 A1 | 1/2007 | Boatman |
| 2007/0043425 A1 | 2/2007 | Hartley et al. |
| 2007/0050011 A1 | 3/2007 | Klein et al. |
| 2007/0055326 A1 | 3/2007 | Farley et al. |
| 2007/0055350 A1 | 3/2007 | Erickson et al. |
| 2007/0055358 A1 | 3/2007 | Krolik et al. |
| 2007/0055360 A1 | 3/2007 | Hanson et al. |
| 2007/0060989 A1 | 3/2007 | Deem et al. |
| 2007/0061002 A1 | 3/2007 | Paul, Jr. et al. |
| 2007/0073373 A1 | 3/2007 | Bonsignore |
| 2007/0088425 A1 | 4/2007 | Schaeffer |
| 2007/0112344 A1 | 5/2007 | Keilman |
| 2007/0135677 A1 | 6/2007 | Miller et al. |
| 2007/0142896 A1 | 6/2007 | Anderson et al. |
| 2007/0150051 A1 | 6/2007 | Arnault De La Menardiere et al. |
| 2007/0156167 A1 | 7/2007 | Connors et al. |
| 2007/0162104 A1 | 7/2007 | Frid |
| 2007/0167898 A1 | 7/2007 | Peters et al. |
| 2007/0167955 A1 | 7/2007 | Arnault De La Menardiere et al. |
| 2007/0168013 A1 | 7/2007 | Douglas |
| 2007/0168018 A1 | 7/2007 | Amplatz et al. |
| 2007/0179598 A1 | 8/2007 | Duerig |
| 2007/0185565 A1 | 8/2007 | Schwammenthal et al. |
| 2007/0207186 A1 | 9/2007 | Scanlon et al. |
| 2007/0208410 A1 | 9/2007 | Berra et al. |
| 2007/0213805 A1 | 9/2007 | Schaeffer et al. |
| 2007/0213807 A1 | 9/2007 | Roubin et al. |
| 2007/0219610 A1 | 9/2007 | Israel |
| 2007/0219627 A1 | 9/2007 | Chu et al. |
| 2007/0225797 A1 | 9/2007 | Krivoruhko |
| 2007/0233229 A1 | 10/2007 | Berra et al. |
| 2007/0237973 A1 | 10/2007 | Purdy et al. |
| 2007/0244542 A1 | 10/2007 | Greenan et al. |
| 2007/0244543 A1 | 10/2007 | Mitchell |
| 2007/0244547 A1 | 10/2007 | Greenan |
| 2007/0250154 A1 | 10/2007 | Greenberg et al. |
| 2007/0255388 A1 | 11/2007 | Rudakov et al. |
| 2008/0002871 A1 | 1/2008 | Gunzert-Marx et al. |
| 2008/0015673 A1 | 1/2008 | Chuter |
| 2008/0058918 A1 | 3/2008 | Watson |
| 2008/0109058 A1 | 5/2008 | Greenberg et al. |
| 2008/0109066 A1 | 5/2008 | Quinn |
| 2008/0114444 A1 | 5/2008 | Yu |
| 2008/0114445 A1 | 5/2008 | Melsheimer et al. |
| 2008/0147173 A1 | 6/2008 | Mciff et al. |
| 2008/0167704 A1 | 7/2008 | Wright et al. |
| 2008/0195190 A1 | 8/2008 | Bland et al. |
| 2008/0195191 A1 | 8/2008 | Luo et al. |
| 2008/0215134 A1 | 9/2008 | Lawrence-Brown |
| 2008/0249598 A1 | 10/2008 | Sherry |
| 2008/0262595 A1 | 10/2008 | Chu et al. |
| 2008/0269789 A1 | 10/2008 | Eli |
| 2008/0275540 A1 | 11/2008 | Wen |
| 2008/0275542 A1 | 11/2008 | LaDuca et al. |
| 2008/0288044 A1 | 11/2008 | Osborne |
| 2008/0294234 A1 | 11/2008 | Hartley et al. |
| 2008/0300665 A1 | 12/2008 | Lootz et al. |
| 2008/0319528 A1 | 12/2008 | Yribarren et al. |
| 2009/0012597 A1 | 1/2009 | Doig et al. |
| 2009/0012602 A1 | 1/2009 | Quadri |
| 2009/0030497 A1 | 1/2009 | Metcalf et al. |
| 2009/0030502 A1 | 1/2009 | Sun et al. |
| 2009/0048663 A1 | 2/2009 | Greenberg |
| 2009/0054967 A1 | 2/2009 | Das |
| 2009/0062899 A1 | 3/2009 | Dang et al. |
| 2009/0069881 A1 | 3/2009 | Chalekian et al. |
| 2009/0069882 A1 | 3/2009 | Venturelli et al. |
| 2009/0082841 A1 | 3/2009 | Zacharias et al. |
| 2009/0082847 A1 | 3/2009 | Zacharias et al. |
| 2009/0099648 A1 | 4/2009 | Yu |
| 2009/0099649 A1 | 4/2009 | Chobotov et al. |
| 2009/0099650 A1 | 4/2009 | Bolduc et al. |
| 2009/0105809 A1 | 4/2009 | Lee et al. |
| 2009/0112233 A1 | 4/2009 | Xiao |
| 2009/0125096 A1 | 5/2009 | Chu et al. |
| 2009/0138067 A1 | 5/2009 | Pinchuk et al. |
| 2009/0149877 A1 | 6/2009 | Hanson et al. |
| 2009/0164001 A1 | 6/2009 | Biggs et al. |
| 2009/0171437 A1 | 7/2009 | Brocker et al. |

(56) References Cited

U.S. PATENT DOCUMENTS

| | | |
|---|---|---|
| 2009/0192587 A1 | 7/2009 | Frid |
| 2009/0227997 A1 | 9/2009 | Wang et al. |
| 2009/0240316 A1 | 9/2009 | Bruszewski |
| 2009/0248134 A1 | 10/2009 | Dierking et al. |
| 2009/0254170 A1 | 10/2009 | Hartley et al. |
| 2009/0259290 A1 | 10/2009 | Bruszewski et al. |
| 2009/0287145 A1 | 11/2009 | Cragg et al. |
| 2010/0004728 A1 | 1/2010 | Rao et al. |
| 2010/0029608 A1 | 2/2010 | Finley et al. |
| 2010/0063575 A1 | 3/2010 | Shalev et al. |
| 2010/0070019 A1 | 3/2010 | Shalev |
| 2010/0082091 A1 | 4/2010 | Berez et al. |
| 2010/0161026 A1 | 6/2010 | Brocker et al. |
| 2010/0211159 A1 | 8/2010 | Schmid et al. |
| 2010/0249899 A1 | 9/2010 | Chuter et al. |
| 2010/0256725 A1 | 10/2010 | Rasmussen |
| 2010/0274187 A1 | 10/2010 | Argentine |
| 2010/0274345 A1 | 10/2010 | Rust |
| 2010/0292774 A1 | 11/2010 | Shalev |
| 2010/0318171 A1 | 12/2010 | Porter et al. |
| 2011/0040369 A1 | 2/2011 | Rasmussen et al. |
| 2011/0093002 A1 | 4/2011 | Rucker et al. |
| 2011/0125251 A1 | 5/2011 | Cottone et al. |
| 2011/0208289 A1 | 8/2011 | Shalev |
| 2011/0208296 A1 | 8/2011 | Duffy et al. |
| 2011/0208297 A1 | 8/2011 | Tuval et al. |
| 2011/0208298 A1 | 8/2011 | Tuval et al. |
| 2011/0218607 A1 | 9/2011 | Arbefeuille et al. |
| 2011/0257720 A1 | 10/2011 | Peterson et al. |
| 2011/0262684 A1 | 10/2011 | Wintsch et al. |
| 2011/0264184 A1 | 10/2011 | Heltai |
| 2011/0288622 A1 | 11/2011 | Chan et al. |
| 2011/0301702 A1 | 12/2011 | Rust et al. |
| 2011/0319983 A1 | 12/2011 | Zhu et al. |
| 2012/0150274 A1 | 6/2012 | Shalev et al. |
| 2012/0172929 A1 | 7/2012 | Shalev |
| 2012/0179236 A1 | 7/2012 | Benary et al. |
| 2012/0185031 A1 | 7/2012 | Ryan et al. |
| 2012/0271401 A1 | 10/2012 | Bruszewski et al. |
| 2012/0310324 A1 | 12/2012 | Benary et al. |
| 2012/0316634 A1 | 12/2012 | Shalev et al. |
| 2012/0323305 A1 | 12/2012 | Benary et al. |
| 2012/0330399 A1 | 12/2012 | Shalev et al. |
| 2012/0330401 A1 | 12/2012 | Sugimoto et al. |
| 2013/0013050 A1 | 1/2013 | Shalev et al. |
| 2013/0013051 A1 | 1/2013 | Benary |
| 2013/0035751 A1 | 2/2013 | Shalev |
| 2013/0090722 A1 | 4/2013 | Shalev et al. |
| 2013/0116773 A1 | 5/2013 | Roeder et al. |
| 2013/0116775 A1 | 5/2013 | Roeder et al. |
| 2013/0131783 A1 | 5/2013 | Shalev et al. |
| 2013/0204343 A1 | 8/2013 | Shalev |
| 2013/0261994 A1 | 10/2013 | Raz et al. |
| 2013/0289587 A1 | 10/2013 | Shalev |
| 2013/0297005 A1 | 11/2013 | Shalev |
| 2014/0005764 A1 | 1/2014 | Schroeder |
| 2014/0052236 A1 | 2/2014 | Shalev |
| 2014/0148888 A1 | 5/2014 | Barrand |
| 2014/0172072 A1 | 6/2014 | Shalev |
| 2014/0180378 A1 | 6/2014 | Roeder |
| 2014/0288635 A1 | 9/2014 | Shalev |
| 2014/0324154 A1 | 10/2014 | Shalev |
| 2015/0196301 A1 | 7/2015 | Bödewadt et al. |
| 2015/0374383 A1 | 12/2015 | Bödewadt et al. |
| 2016/0262880 A1 | 9/2016 | Li et al. |

FOREIGN PATENT DOCUMENTS

| | | |
|---|---|---|
| CN | 2817770 | 9/2006 |
| CN | 201058061 | 5/2008 |
| EP | 1177780 | 2/2002 |
| EP | 1325716 | 7/2003 |
| EP | 1470797 | 10/2004 |
| EP | 1759666 | 3/2007 |
| EP | 1961401 | 8/2008 |
| EP | 2266509 | 12/2010 |
| EP | 2298248 | 3/2011 |
| JP | 2002253682 | 9/2002 |
| WO | 98/06355 | 2/1998 |
| WO | 9934748 | 7/1999 |
| WO | 0152776 A1 | 7/2001 |
| WO | 02083038 | 10/2002 |
| WO | 03099108 | 12/2003 |
| WO | 2004017868 | 3/2004 |
| WO | 2004100836 A1 | 11/2004 |
| WO | 2005002466 | 1/2005 |
| WO | 2005034809 A1 | 4/2005 |
| WO | 2005037138 | 4/2005 |
| WO | 2005041781 | 5/2005 |
| WO | 2005041783 | 5/2005 |
| WO | 2005046524 | 5/2005 |
| WO | 2005046526 A1 | 5/2005 |
| WO | 2006007389 | 1/2006 |
| WO | 2006028925 | 3/2006 |
| WO | 2006040372 | 7/2006 |
| WO | 2006088905 A1 | 8/2006 |
| WO | 2006130755 A2 | 12/2006 |
| WO | 2007022495 | 2/2007 |
| WO | 2007039587 | 4/2007 |
| WO | 2007084547 | 7/2007 |
| WO | 2007144782 | 12/2007 |
| WO | 2008008291 | 1/2008 |
| WO | 2008035337 | 3/2008 |
| WO | 2008042266 | 4/2008 |
| WO | 2008047092 | 4/2008 |
| WO | 2008047354 | 4/2008 |
| WO | 2008051704 A1 | 5/2008 |
| WO | 2008053469 | 5/2008 |
| WO | 2008066923 | 6/2008 |
| WO | 2008107885 | 9/2008 |
| WO | 2008140796 | 11/2008 |
| WO | 2009078010 | 6/2009 |
| WO | 2009116041 | 9/2009 |
| WO | 2009116042 | 9/2009 |
| WO | 2009118733 | 10/2009 |
| WO | 2010/027704 | 3/2010 |
| WO | 2010024869 | 3/2010 |
| WO | 2010024879 | 3/2010 |
| WO | 2010031060 | 3/2010 |
| WO | 2010045238 | 4/2010 |
| WO | 2010062355 | 6/2010 |
| WO | 2010088776 | 8/2010 |
| WO | 2010128162 | 11/2010 |
| WO | 2010150208 | 12/2010 |
| WO | 2011004374 | 1/2011 |
| WO | 2011007354 | 1/2011 |
| WO | 2011055364 | 5/2011 |
| WO | 2011064782 | 6/2011 |
| WO | 2011067764 | 6/2011 |
| WO | 2011070576 | 6/2011 |
| WO | 2011080738 | 7/2011 |
| WO | 2011095979 | 8/2011 |
| WO | 2011106532 | 9/2011 |
| WO | 2011106533 | 9/2011 |
| WO | 2011106544 | 9/2011 |
| WO | 2012049679 | 4/2012 |
| WO | 2012104842 | 8/2012 |
| WO | 2012111006 | 8/2012 |
| WO | 2012117395 | 9/2012 |
| WO | 2012176187 | 12/2012 |
| WO | 2013005207 | 1/2013 |
| WO | 2013030818 | 3/2013 |
| WO | 2013030819 | 3/2013 |
| WO | 2013065040 | 5/2013 |
| WO | 2013084235 | 6/2013 |
| WO | 2013171730 | 11/2013 |
| WO | 2014020609 | 2/2014 |
| WO | 2014108895 | 7/2014 |

(56) References Cited

FOREIGN PATENT DOCUMENTS

| WO | 2014141232 | 9/2014 |
|---|---|---|
| WO | 2014188412 | 11/2014 |

OTHER PUBLICATIONS

European search report issued in Application No. 10834308.8, dated Sep. 22, 2016.
A non-final Office Action issued on Feb. 28, 2014 in U.S. Appl. No. 13/512,778.
An International Preliminary Report on Patentability dated Jan. 7, 2014, which issued during the prosecution of Applicant's PCT/IL2012/000269.
An International Preliminary Report on Patentability dated Jan. 4, 2012, which issued during the prosecution of Applicant's PCT/IB2010/052861.
An International Preliminary Report on Patentability dated Dec. 23, 2013, which issued during the prosecution of Applicant's PCT/IL2012/000241.
An International Preliminary Report on Patentability dated Aug. 6, 2013, which issued during the prosecution of Applicant's PCT/IL2012/000060.
An English translation of an Office Action dated Oct. 8, 2014, which issued during the prosecution of Chinese Patent Application No. 201080036970.7.
An English translation of an Office Action dated Nov. 28, 2013, which issued during the prosecution of Chinese Patent Application No. 200880126889.0.
An English translation of an Office Action dated Jan. 28, 2014, which issued during the prosecution of Chinese Patent Application No. 201080036970.7.
An English translation of an Office Action dated May 16, 2014, which issued during the prosecution of Chinese Patent Application No. 200880126889.0.
An English translation of an Office Action dated Aug. 25, 2011, which issued during the prosecution of Chinese Patent Application No. 200880014919.9.
An English translation of an Office Action dated Feb. 16, 2013, which issued during the prosecution of Chinese Patent Application No. 200880126889.0.
An International Preliminary Report on Patentability dated Jan. 10, 2012, which issued during the prosecution of Applicant's PCT/IL2010/000549.
An International Preliminary Report on Patentability dated Jan. 17, 2012, which issued during the prosecution of Applicant's PCT/IL2010/000564.
A Notice of Allowance dated Aug. 2, 2012, which issued during the prosecution of U.S. Appl. No. 12/529,936.
An Advisory Action dated Feb. 13, 2014, which issued during the prosecution of Applicant's U.S. Appl. No. 13/807,880.
An International Preliminary Report on Patentability dated Jun. 5, 2012, which issued during the prosecution of Applicant's PCT/IL2010/000999.
An International Preliminary Report on Patentability dated Jun. 5, 2012, which issued during the prosecution of Applicant's PCT/IL2010/001018.
An International Preliminary Report on Patentability dated Jun. 10, 2014, which issued during the prosecution of Applicant's PCT/IL2012/050506.
A Notice of Allowance issued in U.S. Appl. No. 13/807,906 on Oct. 10, 2014.
A Restriction Requirement dated Jan. 29, 2014, which issued during the prosecution of U.S. Appl. No. 13/519,971.
An International Preliminary Report on Patentability dated Jun. 12, 2012, which issued during the prosecution of Applicant's PCT/IL2010/001037.
An International Preliminary Report on Patentability dated Mar. 4, 2014, which issued during the prosecution of Applicant's PCT/IL2012/000300.
An International Preliminary Report on Patentability dated May 6, 2014, which issued during the prosecution of Applicant's PCT/IL2012/050424.
An International Preliminary Report on Patentability dated May 8, 2012, which issued during the prosecution of Applicant's PCT/IL2010/000917.
An International Preliminary Report on Patentability dated Nov. 18, 2014, which issued during the prosecution of Applicant's PCT/IL2012/000190.
An International Search Report and a Written Opinion both dated Apr. 18, 2011, which issued during the prosecution of Applicant's PCT/IL2010/001037.
An International Search Report and a Written Opinion both dated Aug. 4, 2011, which issued during the prosecution of Applicant's PCT/IL2010/000999.
An International Search Report and a Written Opinion both dated Aug. 31, 2012, which issued during the prosecution of Applicant's PCT/IL2012/000148.
An International Search Report and a Written Opinion both dated Dec. 3, 2010, which issued during the prosecution of Applicant's PCT/IL2010/000564.
An International Search Report and a Written Opinion both dated Feb. 4, 2011, which issued during the prosecution of Applicant's PCT/IB2010/052861.
An International Search Report and a Written Opinion both dated Jul. 13, 2012, which issued during the prosecution of Applicant's PCT/IL2012/000083.
An International Search Report and a Written Opinion both dated Jul. 17, 2012, which issued during the prosecution of Applicant's PCT/IL2012/000095.
An International Search Report and a Written Opinion both dated Jun. 14, 2013, which issued during the prosecution of Applicant's PCT/IL2012/050506.
An International Search Report and a Written Opinion both dated Jun. 28, 2011, which issued during the prosecution of Applicant's PCT/IL2011/000135.
An International Search Report and a Written Opinion both dated Jun. 30, 2009, which issued during the prosecution of Applicant's PCT/IL2008/001621.
An International Search Report and a Written Opinion both dated Mar. 10, 2011, which issued during the prosecution of Applicant's PCT/IL2010/000917.
An International Search Report and a Written Opinion both dated Mar. 11, 2009, which issued during the prosecution of Applicant's PCT/IL2007/001312.
An International Search Report and a Written Opinion both dated Mar. 15, 2013, which issued during the prosecution of Applicant's PCT/IL2012/050424.
An International Preliminary Report on Patentability dated Sep. 3, 2013, which issued during the prosecution of Applicant's PCT/IL2012/000095.
An International Search Report and a Written Opinion both dated Mar. 30, 2011, which issued during the prosecution of Applicant's PCT/IL2010/001018.
An International Search Report and a Written Opinion both dated May 23, 2011, which issued during the prosecution of Applicant's PCT/IL2010/001087.
An International Search Report and a Written Opinion both dated Nov. 5, 2010, which issued during the prosecution of Applicant's PCT/IL2010/000549.
An International Search Report and a Written Opinion both dated Nov. 27, 2012, which issued during the prosecution of Applicant's PCT/IL2012/000300.
An International Search Report and a Written Opinion both dated Oct. 1, 2012, which issued during the prosecution of Applicant's PCT/IL2012/000241.
An International Search Report and a Written Opinion both dated Oct. 4, 2012, which issued during the prosecution of Applicant's PCT/IL2012/000269.
An International Search Report and a Written Opinion both dated Sep. 6, 2012, which issued during the prosecution of Applicant's PCT/IL2012/000190.

(56) References Cited

OTHER PUBLICATIONS

An International Search Report and a Written Opinion both dated Apr. 28, 2014, which issued during the prosecution of Applicant's PCT/IL2014/050019.
An International Search Report dated Jul. 30, 2014, which issued during the prosecution of Applicant's PCT/IL2014/050174.
An International Search Report and a Written Opinion both dated Sep. 24, 2012, which issued during the prosecution of Applicant's PCT/IL2012/000060.
An International Search Report and a Written Opinion both dated Sep. 29, 2008, which issued during the prosecution of Applicant's PCT/IL2008/000287.
An International Search Report dated Nov. 26, 2013, which issued during the prosecution of Applicant's PCT/IL2013/050656.
Notice of allowance dated Jun. 24, 2014, which issued during the prosecution of Applicant's U.S. Appl. No. 13/380,278.
An International Search Report dated Nov. 28, 2014, which issued during the prosecution of Applicant's PCT/IL2014/050434.
An Interview Summary dated Feb. 28, 2012, which issued during the prosecution of U.S. Appl. No. 12/529,936.
An Office Action dated Apr. 10, 2014, which issued during the prosecution of Applicant's U.S. Appl. No. 13/807,906.
An Office Action dated Apr. 24, 2014, which issued during the prosecution of Applicant's U.S. Appl. No. 13/380,278.
An Office Action dated Dec. 2, 2013, which issued during the prosecution of U.S. Appl. No. 13/807,880.
An office Action dated Feb. 25. 2013, which issued during the prosecution of U.S. Appl. No. 13/031,871.
An Office Action dated Feb. 27, 2013, which issued during the prosecution of U.S. Appl. No. 12/808,037.
An Office Action dated Jul. 24, 2014, which issued during the prosecution of Canadian Patent Application No. 2768228.
An Office Action dated Jul. 28, 2014, which issued during the prosecution of U.S. Appl. No. 13/031,871.
An Office Action dated Jun. 19, 2012, which issued during the prosecution of U.S. Appl. No. 12/808,037.
An Office Action dated Mar. 24, 2011, which issued during the prosecution of U.S. Appl. No. 12/529,936.
An Office Action dated Mar. 28, 2014, which issued during the prosecution of Applicant's U.S. Appl. No. 13/519,971.
An Office Action dated Apr. 27, 2011, which issued during the prosecution of U.S. Appl. No. 12/447,684.
An Office Action dated Apr. 28, 2014, which issued during the prosecution of Applicant's U.S. Appl. No. 13/939,798.
An Office Action dated May 20, 2013, which issued during the prosecution of U.S. Appl. No. 13/807,880.
An Office Action dated Nov. 12, 2010, which issued during the prosecution of U.S. Appl. No. 12/447,684.
An Office Action dated Nov. 3, 2014, which issued during the prosecution of Canadian Patent Application No. 2767596.
An Office Action dated Nov. 19, 2013, which issued during the prosecution of U.S. Appl. No. 13/663,117.
An Office Action dated Oct. 11, 2012, which issued during the prosecution of U.S. Appl. No. 13/031,871.
U.S. Appl. No. 61/219,758, filed Jun. 23, 2009.
U.S. Appl. No. 61/221,074, filed Jun. 28, 2009.
U.S. Appl. No. 61/496,613, filed Jun. 14, 2011.
An Office Action dated Oct. 28, 2011, which issued during the prosecution of U.S. Appl. No. 12/529,936.
U.S. Appl. No. 61/505,132, filed Jul. 7, 2011.
U.S. Appl. No. 61/678,182, filed Aug. 1, 2012.
U.S. Appl. No. 61/529,931, filed Sep. 1, 2011.
U.S. Appl. No. 61/553,209, filed Oct. 30, 2011.
U.S. Appl. No. 61/499,195, filed Jun. 21, 2011.
U.S. Appl. No. 61/749,965, filed Jan. 8, 2013.
Notice of Allowance dated Jun. 18, 2013, which issued during the prosecution of U.S. Appl. No. 13/523,296.
Office Action issued on Oct. 27, 2014 in Canadian Patent Application No. 2,785,953.

Ryhanen J., in "Biocompatibility evaluation of nickel-titanium shape memory metal alloy," Academic Dissertation, Faculty of Medicine, Department of Surgery, University of Oulu, Finland (May 1999).
Supplementary European Search Report dated Dec. 13, 2012, which issued during the prosecution of Applicant's European App No. 08719912.1.
Supplementary European Search Report dated Feb. 17, 2014, which issued during the prosecution of Applicant's European App No. 12803376.8.
Supplementary European Search Report dated Jun. 23, 2014, which issued during the prosecution of Applicant's European App No. 12741804.4.
Written Opinion dated Nov. 26, 2013, which issued during the prosecution of Applicant's PCT/IL2013/050656.
"E-vita® open plus" product brochure (JOTEC GmbH, Hechingen, Germany), 2010.
An Office action dated Sep. 4, 2014, from the U.S. Patent and Trademark Office in counterpart U.S. Appl. No. 13/519,971.
European Office Action issued Dec. 17, 2014 in European Patent Application No. 12803376.8.
An Office action dated Feb. 5, 2015, from the U.S. Patent and Trademark Office in counterpart U.S. Appl. No. 13/384,075.
European Search Report issued Feb. 24, 2014 in European Patent Application No. 12803376.8.
Fattori et al., Degenerative aneurysm of the descending aorta. Endovascular Treatment. pp. 1-11, 2007, European Association for Cardio-Thoracic Surgery.
International Preliminary Report on Patentability dated Jan. 12, 2010 in corresponding International Application No. PCT/IL2008/000287.
Fonseca A et al., "Intravascular ultrasound assessment of the novel AngioSculpt scoring balloon catheter for the treatment of complex coronary lesions," J Invasive Cardiol 20(1):21-7 (Jan. 2008).
Van Prehn J et al., "Oversizing of aortic stent grafts for abdominal aneurysm repair: a systematic review of the benefits and risks," Eur J Vase Endovase Surg. Jul. 2009:38(I):42-53. Epub May 9, 2009 (abstract only).
Invitation to Pay Additional Fees dated May 13, 2014, which issued during the prosecution of Applicant's PCT/IL2014/050019.
Invitation to Pay Additional Fees dated May 8, 2014, which issued during the prosecution of Applicant's PCT/IL2014/50174.
Khlif H et al., "Contribution to the Improvement of Textile Vascular Prostheses Crimping," Trends in Applied Sciences Research 6(9):1019-1027 (2011).
U.S. Appl. No. 61/775,964, filed Mar. 11, 2013.
U.S. Appl. No. 61/826,544, filed May 23, 2013.
U.S. Appl. No. 61/906,014, filed Nov. 19, 2013.
U.S. Appl. No. 61/926,533, filed Jan. 13, 2014.
U.S. Appl. No. 61/528,242, filed Aug. 28, 2011.
An Office Action dated Aug. 15, 2014, which issued during the prosecution of Applicant's U.S. Appl. No. 13/939,798.
U.S. Appl. No. 61/566,654, filed Dec. 4, 2011.
An English translation of an Office Action dated Mar. 19, 2015, which issued during the prosecution of Chinese Patent Application No. 201080036970.7.
A Notice of Allowance dated Jan. 20, 2015, which issued during the prosecution of U.S. Appl. No. 13/383,128.
A Notice of Allowance dated Nov. 7, 2014, which issued during the prosecution of U.S. Appl. No. 13/512,778.
An Office Action dated Aug. 15, 2014, which issued during the prosecution of U.S. Appl. No. 13/512,778.
An International Search Report and a Written Opinion both dated Mar. 18, 2015, which issued during the prosecution of Applicant's PCT/IL2014/050973.
An Office Action dated Apr. 14, 2015, which issued during the prosecution of U.S. Appl. No. 14/130,213.
An International Preliminary Report on Patentability dated Feb. 3, 2015, which issued during the prosecution of Applicant's PCT/IL2013/050656.
A Notice of Allowance dated Jan. 7, 2014, which issued during the prosecution of U.S. Appl. No. 13/663,117.

(56) References Cited

OTHER PUBLICATIONS

An Office Action dated Mar. 26, 2015, which issued during the prosecution of U.S. Appl. No. 13/514,240.
Supplementary European Search Report dated Oct. 31, 2014, which issued during the prosecution of Applicant's European App No. 12752054.2.
An Office Action dated Sep. 2, 2014, which issued during the prosecution of U.S. Appl. No. 12/447,684.
U.S. Appl. No. 61/448,199, filed Mar. 2, 2011.
U.S. Appl. No. 61/014,031, filed Dec. 15, 2007.
An Examiner Interview Summary dated Dec. 13, 2010, which issued during the prosecution of U.S. Appl. No. 12/447,684.
An Office Action dated Mar. 21, 2012, which issued during the prosecution of U.S. Appl. No. 12/808,037.
An Office Action dated May 22, 2013, which issued during the prosecution of U.S. Appl. No. 12/808,037.
U.S. Appl. No. 60/863,373, filed Oct. 29, 2006.
An International Preliminary Report on Patentability dated Aug. 21, 2013, which issued during the prosecution of Applicant's PCT/IL2012/000083.

* cited by examiner

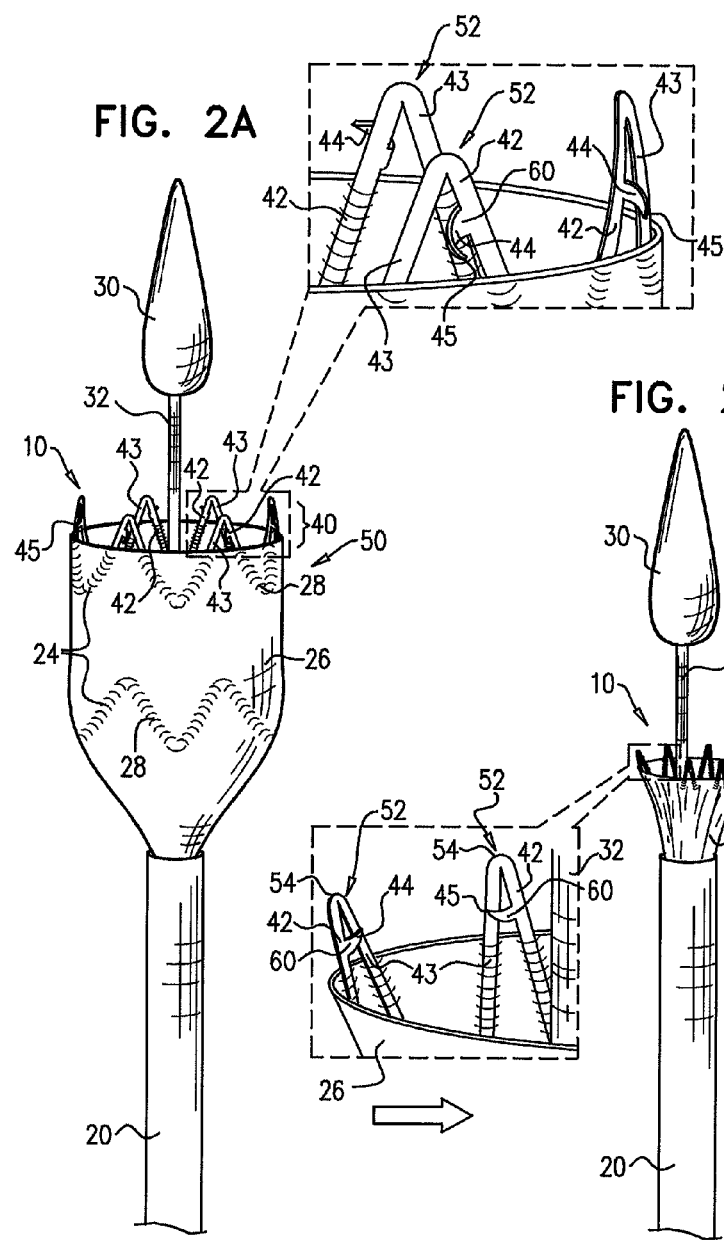

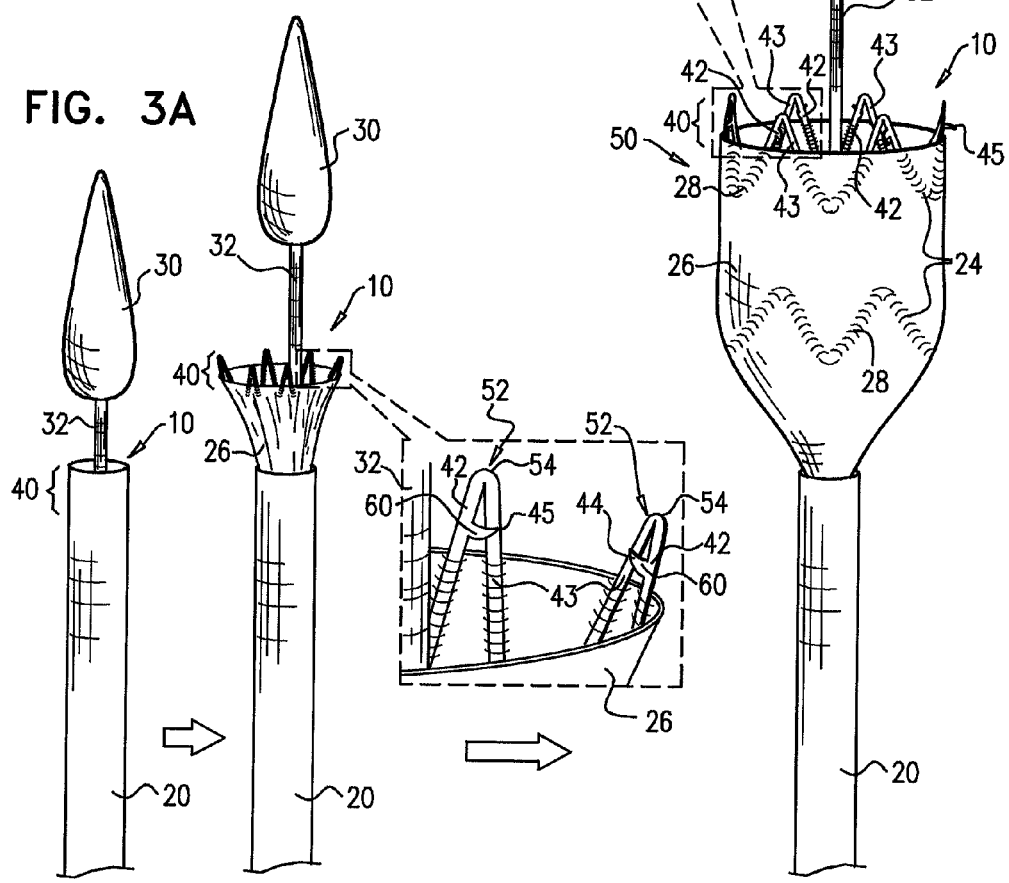

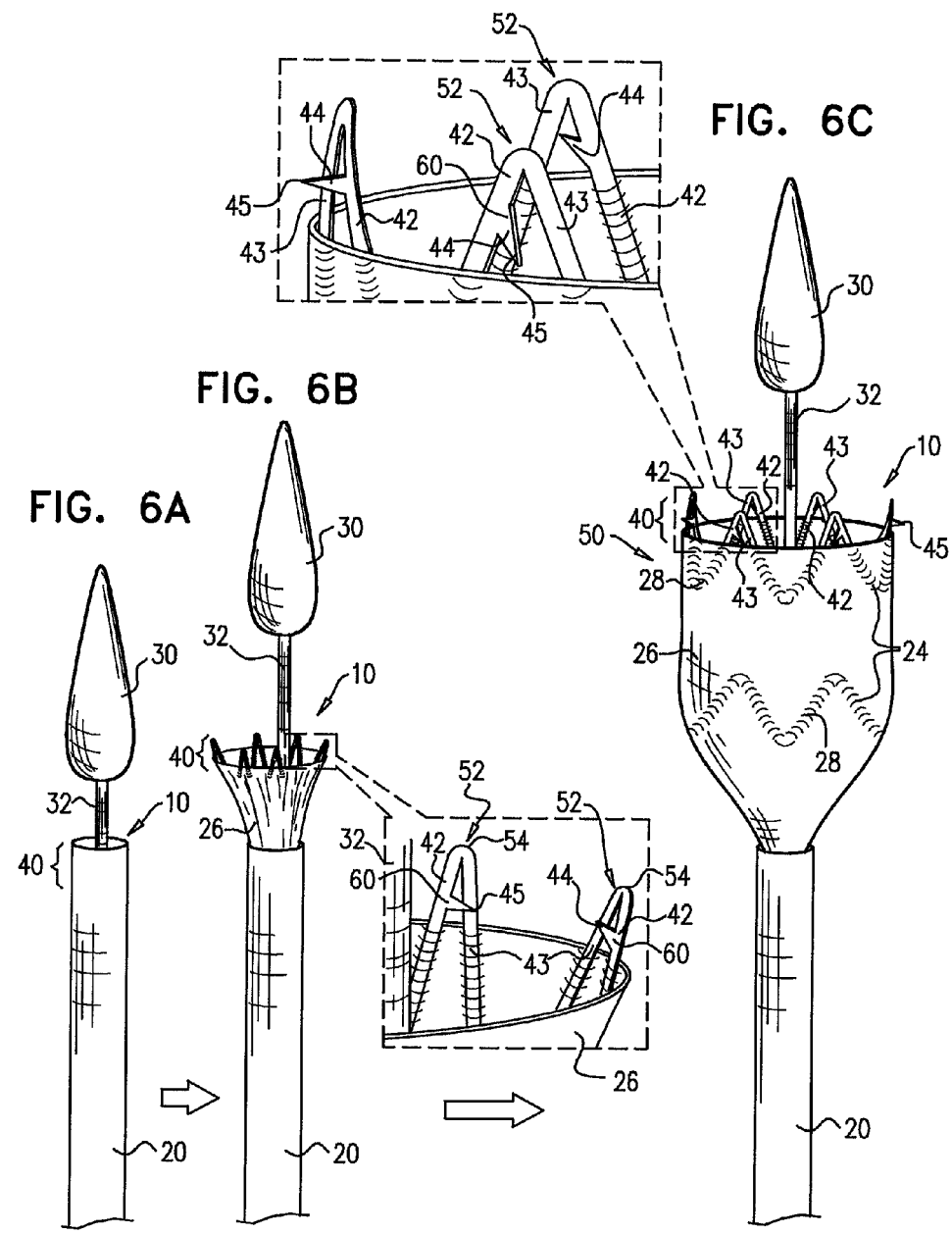

STENT-GRAFT WITH FIXATION ELEMENTS THAT ARE RADIALLY CONFINED FOR DELIVERY

CROSS REFERENCE TO RELATED APPLICATIONS

This application is a National Stage of International Application No. PCT/IL2012/000190 filed May 15, 2012, the contents of all of which are incorporated herein by reference in their entirety.

FIELD OF THE APPLICATION

This present application relates generally to prostheses and surgical methods, and specifically to tubular prostheses, including endovascular stent-grafts, and surgical techniques for using the prostheses to maintain patency of body passages such as blood vessels, and treating aneurysms.

BACKGROUND OF THE APPLICATION

Endovascular prostheses are sometimes used to treat aortic aneurysms. Such treatment includes implanting a stent or stent-graft within the diseased vessel to bypass the anomaly. An aneurysm is a sac formed by the dilation of the wall of the artery. Aneurysms may be congenital, but are usually caused by disease or, occasionally, by trauma. Aortic aneurysms, which commonly form between the renal arteries and the iliac arteries, are referred to as abdominal aortic aneurysms ("AAAs"). Other aneurysms occur in the aorta, such as thoracic aortic aneurysms ("TAAs"), which may occur in one or more of the descending aorta, the ascending aorta, and the aortic arch.

Conventional stent-grafts typically include a radially-expandable stent, formed from a plurality of uniform annular stent springs, and a cylindrically-shaped graft material to which the stent springs are coupled. Stent-grafts may be used for reinforcing or holding open the interior wall of lumens, such as blood vessels.

Some commercially-available stent-grafts utilize a set of circumferentially-disposed proximal barbs in order to facilitate long term fixation of the stent-graft at its appropriate landing zone on the wall of a target body lumen in general, and, in particular, a major artery such as the aorta. An additional role of fixation barbs is to facilitate sealing between the distal end of the graft material and the blood vessel neck, so as to prevent endovascular blood leaks around the stent-graft's distal edge, usually referred to as type I endoleaks.

SUMMARY OF APPLICATIONS

In some applications of the present invention, an endovascular stent-graft is configured to assume a radially-compressed delivery state and a radially-expanded deployment state. The stent-graft comprises a flexible stent member and a tubular fluid flow guide. The fluid flow guide comprises a graft material, and which is attached to the stent member, such that at least a generally circumferential section of the stent member is not covered by the fluid flow guide at least when the stent-graft is in the radially-expanded deployment state. The circumferential section of the stent member is shaped so as to define: (a) a plurality of first struts, (b) a plurality of second struts, and (c) a plurality of fixation members, which are coupled to respective ones of the first struts. The circumferential section is configured such that (a) when the stent-graft is in the delivery state, typically when the body is positioned in an external delivery sheath of a delivery catheter, the second struts radially constrain the fixation members, respectively, from protruding radially outward, and (b) when the stent-graft is in the deployment state, the fixation members are not radially-constrained by the second struts and protrude radially outward.

When the stent-graft is in the delivery state, the radially-constrained fixation members are unlikely to penetrate, tear, or otherwise damage the external delivery sheath of the delivery catheter. When the stent-graft is in the deployment state, the fixation members are configured to penetrate the inner wall of a tubular body part, such as a blood vessel, in order to help anchor stent-graft to the blood vessel.

Reference is made to FIG. 1, which is a schematic illustration of an endovascular stent-graft during several stages of loading the stent-graft into an external delivery sheath of a delivery catheter of a delivery system, in accordance with the prior art. The traumatic nature of fixation barbs presents a technical challenge in reducing the crossing profile and maintaining the integrity of external sheaths of delivery systems of stent-grafts. Fixation barbs, because they are traumatic, are often prone to damage the inner wall of the polymeric external delivery sheath that externally confines the stent-graft when the stent-graft is in its radially compressed state. The external delivery sheath is usually gradually advanced over the stent in the proximal to distal direction, relative to the operator that is crimping the stent-graft into the delivery system. Because most fixation barbs are directed in the distal to proximal direction, pushing an external sheath over the stent in a direction opposite to the direction in which the barbs point is usually traumatic to the inner wall of such an external delivery sheath. To prevent such trauma to the sheath, a resilient and relatively thick external sheath is generally used, which adversely increases the crossing profile of the crimped stent-graft.

Some techniques of the present invention overcome this problem by radially confining at least the traumatic tips of the fixation members from radially outwardly protruding, when the stent-graft is radially confined. When the stent-graft transitions from a radially-confined to a radially-expanded state, the fixation members are released and their traumatic tips assume a radially-protruded position for tissue penetration.

For some applications, the stent member is shaped so as to define a generally circumferential band, which includes the above-mentioned circumferential section and the first and second struts. The circumferential band is shaped such that pairs of first and second struts are coupled at respective peaks of the circumferential band. Typically, the fixation members are shaped so as to define respective bases at respective first ends thereof and respective sharp tips at respective second ends thereof. The bases are coupled to respective ones of the first struts.

For some applications, a first subset of the fixation members extend in a counterclockwise direction from their respective first struts, and a second subset of the fixation members extend in a clockwise direction from their respective first struts. For some applications, the fixation members of the first and second subsets are arranged alternatingly around the circumferential section. This arrangement of the fixation members generally helps better anchor the stent-graft to the wall of the blood vessel. For example, blood flow in tortuous blood vessels may cause some rotation of the blood vessel. Because some fixation members point in each direction (clockwise and counterclockwise), a subset of the fixation members anchors better regardless of the direction in which the blood vessel rotates (clockwise or counterclockwise).

In some applications of the present invention, an alternative configuration of the stent-graft is provided which also overcomes the problem described hereinabove with reference to FIG. 1. In this alternative configuration, the fixation members are outwardly radially convex as viewed from outside the stent-graft, such that when the stent-graft is radially confined, the tips of the fixation members are radially retracted relative to the apex of the convexity of the fixation member. When the stent-graft assumes its radially expanded state, the fixation members are released to their radially protruded position and respective tips thereof assume the outermost radial position.

There is therefore provided, in accordance with an application of the present invention, apparatus including an endovascular stent-graft, which is configured to assume a radially-compressed delivery state and a radially-expanded deployment state, and which includes:

a flexible stent member; and a tubular fluid flow guide, which includes a graft material, and which is attached to the stent member, wherein the stent member includes a generally circumferential section that is shaped so as to define: (a) a plurality of first struts, (b) a plurality of second struts, and (c) a plurality of fixation members, which are coupled to respective ones of the first struts, and wherein the circumferential section is configured such that:

when the stent-graft is in the delivery state, the second struts radially constrain the fixation members, respectively, from protruding radially outward, and when the stent-graft is in the deployment state, the fixation members are not radially-constrained by the second struts and protrude radially outward.

For some applications, a first subset of the fixation members extend in a counterclockwise direction from the respective first struts, and a second subset of the fixation members extend in a clockwise direction from the respective first struts. For some applications, the fixation members of the first subset and the fixation members of the second subset are arranged alternatingly around the circumferential section.

For some applications, the fixation members are shaped as tabs that are cut from the respective first struts on all sides of the tabs except at respective bases of the of fixation members.

For some applications:

the stent member is shaped so as to define a generally circumferential band, which includes the circumferential section and the first and the second struts, and is shaped such that pairs of the first and the second struts are coupled at respective peaks of the circumferential band, the fixation members are shaped so as to define respective bases at respective first ends thereof and respective sharp tips at respective second ends thereof, which bases are coupled to the respective ones of the first struts, and the second struts (a) radially constrain the tips, respectively, from protruding radially outward when the stent-graft is in the radially-compressed delivery state, and (b) do not radially constrain the tips when the stent-graft is in the radially-expanded deployment state.

For some applications, the fixation members are shaped as tabs that are cut from the respective first struts on all sides of the tabs except at respective bases of the of fixation members. For some applications, the peaks are curved. For some applications, the bases of the fixation members are coupled to the respective first struts within a distance of the respective peaks, which distance equals 50% a length of the first struts.

For some applications, a first subset of the pairs of struts are configured such that the first struts thereof are disposed clockwise with respect to the second struts thereof, and a second subset of the pairs of struts are configured such that the first struts thereof are disposed counterclockwise with respect to the second struts thereof. For some applications, the pairs of struts of the first subset and the pairs of struts of the second subset are arranged alternatingly around the circumferential section.

For some applications, the second struts are shaped so as to define respective lateral protrusions, and the lateral protrusions radially constrain the tips, respectively, from protruding radially outward when the stent-graft is in the radially-compressed delivery state, such that the second struts radially constrain the tips, respectively, from protruding radially outward when the stent-graft is in the radially-compressed delivery state. For some applications, one or more of the lateral protrusions include respective radiopaque markers.

For any of the applications described above, the circumferential section may be at least partially not covered by the fluid flow guide at least when the stent-graft is in the radially-expanded deployment state.

For any of the applications described above, when the stent-graft is in the radially-compressed delivery state, (a) a first one of the fixation members may be bent laterally in a clockwise direction, and (b) a second one of the fixation members may be bent laterally in a counterclockwise direction.

For any of the applications described above, when the stent-graft is in the radially-compressed delivery state, (a) a plurality of first ones of the fixation members may be bent laterally in a clockwise direction, (b) a plurality of second ones of the fixation members may be bent laterally in a counterclockwise direction, and the first ones of the fixation members and the second ones of the fixation members may be arranged alternatingly around the circumferential section.

For any of the applications described above, the circumferential section may be disposed at an end of the stent-graft.

For any of the applications described above, the fixation members may be shaped so as to define respective barbs.

For any of the applications described above, the apparatus may further include an external delivery sheath, in which the stent-graft is removably positioned in the radially-compressed delivery state.

There is further provided, in accordance with an application of the present invention, apparatus including an endovascular stent-graft, which is configured to assume a radially-compressed delivery state and a radially-expanded deployment state, and which includes:

a flexible stent member; and a tubular fluid flow guide, which includes a graft material, and which is attached to the stent member, wherein the stent member includes a generally circumferential section that is shaped so as to define at least one fixation member having a sharp tip, wherein, when the stent-graft is in the radially-expanded deployment state, the fixation member protrudes radially outward, and wherein, when the stent-graft is in the radially-compressed delivery state, at least a portion of the fixation member is convex as viewed from outside the stent-graft, such that the sharp tip points radially inward.

For some applications, the stent member is shaped so as to define a generally circumferential band, which includes the circumferential section, which is shaped so as to define at least one first strut and at least one second strut, which are coupled at a peak of the circumferential band, and the fixation member is shaped so as to define a base at a first end thereof and the sharp tip at a second end thereof, which base is coupled to the first strut.

For any of the applications described above, the circumferential section may be at least partially not covered by the fluid flow guide at least when the stent-graft is in the radially-expanded deployment state.

There is still further provided, in accordance with an application of the present invention, a method including:

providing an endovascular stent-graft in a radially-expanded deployment state, which stent-graft includes (a) a flexible stent member, and (b) a tubular fluid flow guide, which includes a graft material, and which is attached to the stent member, wherein the stent member includes a generally circumferential section that is shaped so as to define: (i) a plurality of first struts, (ii) a plurality of second struts, and (iii) a plurality of fixation members, which are coupled to respective ones of the first struts, wherein, when the stent-graft is in the deployment state, the fixation members are not radially-constrained by the second struts and protrude radially outward; and loading the stent-graft into an external delivery sheath of a delivery catheter, such that the stent-graft assumes a radially-compressed delivery state, in which the second struts radially constrain the fixation members, respectively, from protruding radially outward.

For some applications, loading includes: positioning the second struts and the fixation members such that the second struts radially constrain the fixation members, respectively; and, thereafter, loading the fixation members into the external delivery sheath.

For some applications, providing the stent-graft includes providing the stent-graft in which a first subset of the fixation members extend in a counterclockwise direction from the respective first struts, and a second subset of the fixation members extend in a clockwise direction from the respective first struts. For some applications, providing the stent-graft includes providing the stent-graft in which the fixation members of the first subset and the fixation members of the second subset are arranged alternatingly around the circumferential section.

For some applications, providing the stent-graft includes providing the stent-graft in which the fixation members are shaped as tabs that are cut from the respective first struts on all sides of the tabs except at respective bases of the of fixation members.

For some applications, providing the stent-graft includes providing the stent-graft in which:

the stent member is shaped so as to define a generally circumferential band, which includes the circumferential section and the first and the second struts, and is shaped such that pairs of the first and the second struts are coupled at respective peaks of the circumferential band, the fixation members are shaped so as to define respective bases at respective first ends thereof and respective sharp tips at respective second ends thereof, which bases are coupled to the respective ones of the first struts, and the second struts (a) radially constrain the tips, respectively, from protruding radially outward when the stent-graft is in the radially-compressed delivery state, and (b) do not radially constrain the tips when the stent-graft is in the radially-expanded deployment state.

For some applications, providing the stent-graft includes providing the stent-graft in which the fixation members are shaped as tabs that are cut from the respective first struts on all sides of the tabs except at respective bases of the of fixation members. For some applications, providing the stent-graft includes providing the stent-graft in which the peaks are curved. For some applications, providing the stent-graft includes providing the stent-graft in which the bases of the fixation members are coupled to the respective first struts within a distance of the respective peaks, which distance equals 50% of a length of the first struts.

For some applications, providing the stent-graft includes providing the stent-graft in which a first subset of the pairs of struts are configured such that the first struts thereof are disposed clockwise with respect to the second struts thereof, and a second subset of the pairs of struts are configured such that the first struts thereof are disposed counterclockwise with respect to the second struts thereof. For some applications, providing the stent-graft includes providing the stent-graft in which the pairs of struts of the first subset and the pairs of struts of the second subset are arranged alternatingly around the circumferential section.

For some applications, providing the stent-graft includes providing the stent-graft in which the second struts are shaped so as to define respective lateral protrusions, and the lateral protrusions radially constrain the tips, respectively, from protruding radially outward when the stent-graft is in the radially-compressed delivery state, such that the second struts radially constrain the tips, respectively, from protruding radially outward when the stent-graft is in the radially-compressed delivery state.

For any of the applications described above, providing the stent-graft may include providing the stent-graft in which, when the stent-graft is in the radially-compressed delivery state, (a) a first one of the fixation members is bent laterally in a clockwise direction, and (b) a second one of the fixation members is bent laterally in a counterclockwise direction.

For any of the applications described above, providing the stent-graft may include providing the stent-graft in which, when the stent-graft is in the radially-compressed delivery state, (a) a plurality of first ones of the fixation members are bent laterally in a clockwise direction, (b) a plurality of second ones of the fixation members are bent laterally in a counterclockwise direction, and the first ones of the fixation members and the second ones of the fixation members are arranged alternatingly around the circumferential section.

For any of the applications described above, providing the stent-graft may include providing the stent-graft in which the circumferential section is at least partially not covered by the fluid flow guide at least when the stent-graft is in the radially-expanded deployment state.

For any of the applications described above, providing the stent-graft may include providing the stent-graft in which the circumferential section is disposed at an end of the stent-graft.

For any of the applications described above, providing the stent-graft includes providing the stent-graft in which the fixation members are shaped so as to define respective barbs.

There is yet additionally provided, in accordance with an application of the present invention, a method including:

providing an endovascular stent-graft, which is configured to assume a radially-compressed delivery state and a radially-expanded deployment state, and which includes (a) a flexible stent member, and (b) a tubular fluid flow guide, which includes a graft material, and which is attached to the stent member, wherein the stent member includes a generally circumferential section that is shaped so as to define: (i)

a plurality of first struts, (ii) a plurality of second struts, and (iii) a plurality of fixation members, which are coupled to respective ones of the first struts;

transvascularly introducing the stent-graft into a blood vessel of a human subject while the stent-graft is in the radially-compressed delivery state, in which the second struts radially constrain the fixation members, respectively, from protruding radially outward; and thereafter, transitioning the stent-graft in the blood vessel to the radially-expanded deployment state, in which the fixation members are not radially-constrained by the second struts and protrude radially outwardly and engage a wall of the blood vessel.

For some applications, providing the stent-graft includes providing the stent-graft in which the circumferential section is at least partially not covered by the fluid flow guide at least when the stent-graft is in the radially-expanded deployment state.

For some applications, providing the stent-graft includes providing the stent-graft in which a first subset of the fixation members extend in a counterclockwise direction from the respective first struts, and a second subset of the fixation members extend in a clockwise direction from the respective first struts. For some applications, providing the stent-graft includes providing the stent-graft in which the fixation members of the first subset and the fixation members of the second subset are arranged alternatingly around the circumferential section.

For some applications, providing the stent-graft includes providing the stent-graft in which the fixation members are shaped as tabs that are cut from the respective first struts on all sides of the tabs except at respective bases of the of fixation members.

For some applications, providing the stent-graft includes providing the stent-graft in which:

the stent member is shaped so as to define a generally circumferential band, which includes the circumferential section and the first and the second struts, and is shaped such that pairs of the first and the second struts are coupled at respective peaks of the circumferential band, the fixation members are shaped so as to define respective bases at respective first ends thereof and respective sharp tips at respective second ends thereof, which bases are coupled to the respective ones of the first struts, and the second struts (a) radially constrain the tips, respectively, from protruding radially outward when the stent-graft is in the radially-compressed delivery state, and (b) do not radially constrain the tips when the stent-graft is in the radially-expanded deployment state.

For some applications, providing the stent-graft includes providing the stent-graft in which the fixation members are shaped as tabs that are cut from the respective first struts on all sides of the tabs except at respective bases of the of fixation members.

For some applications, providing the stent-graft includes providing the stent-graft in which the peaks are curved.

For some applications, providing the stent-graft includes providing the stent-graft in which the bases of the fixation members are coupled to the respective first struts within a distance of the respective peaks, which distance equals 50% of a length of the first struts.

For some applications, providing the stent-graft includes providing the stent-graft in which a first subset of the pairs of struts are configured such that the first struts thereof are disposed clockwise with respect to the second struts thereof, and a second subset of the pairs of struts are configured such that the first struts thereof are disposed counterclockwise with respect to the second struts thereof. For some applications, providing the stent-graft includes providing the stent-graft in which the pairs of struts of the first subset and the pairs of struts of the second subset are arranged alternatingly around the circumferential section.

For some applications, providing the stent-graft includes providing the stent-graft in which the second struts are shaped so as to define respective lateral protrusions, and the lateral protrusions radially constrain the tips, respectively, from protruding radially outward when the stent-graft is in the radially-compressed delivery state, such that the second struts radially constrain the tips, respectively, from protruding radially outward when the stent-graft is in the radially-compressed delivery state.

For some applications, providing the stent-graft includes providing the stent-graft in which, when the stent-graft is in the radially-compressed delivery state, (a) a first one of the fixation members is bent laterally in a clockwise direction, and (b) a second one of the fixation members is bent laterally in a counterclockwise direction.

For some applications, providing the stent-graft includes providing the stent-graft in which, when the stent-graft is in the radially-compressed delivery state, (a) a plurality of first ones of the fixation members are bent laterally in a clockwise direction, (b) a plurality of second ones of the fixation members are bent laterally in a counterclockwise direction, and the first ones of the fixation members and the second ones of the fixation members are arranged alternatingly around the circumferential section.

For some applications, providing the stent-graft includes providing the stent-graft in which the circumferential section is disposed at an end of the stent-graft.

For some applications, providing the stent-graft includes providing the stent-graft in which the fixation members are shaped so as to define respective barbs.

For some applications, transvascularly introducing includes transvascularly introducing the stent-graft into the blood while the stent-graft is positioned in an external delivery sheath of a delivery catheter in the radially-compressed delivery state, and transitioning the stent-graft to the radially-expanded deployment state in the blood vessel includes deploying the stent-graft from the external delivery sheath.

There is also provided, in accordance with an application of the present invention, a method including:

providing an endovascular stent-graft in a radially-expanded deployment state, which stent-graft includes (a) a flexible stent member, and (b) a tubular fluid flow guide, which includes a graft material, and which is attached to the stent member, wherein the stent member includes a generally circumferential section that is shaped so as to define at least one fixation member having a sharp tip, and wherein, when the stent-graft is in the deployment state, the fixation members protrudes radially outward; and loading the stent-graft into an external delivery sheath of a delivery catheter, such that the stent-graft assumes a radially-compressed delivery state, in which at least a portion of the fixation member is convex as viewed from outside the stent-graft, such that the sharp tip points radially inward.

For some applications, providing the stent-graft includes providing the stent-graft in which the circumferential section is at least partially not covered by the fluid flow guide at least when the stent-graft is in the radially-expanded deployment state.

For some applications, providing the stent-graft includes providing the stent-graft in which the stent member is shaped so as to define a generally circumferential band, which includes the circumferential section, which is shaped so as to define at least one first strut and at least one second strut, which are coupled at a peak of the circumferential band, and the fixation member is shaped so as to define a base at a first end thereof and the sharp tip at a second end thereof, which base is coupled to the first strut.

There is further provided, in accordance with an application of the present invention, a method including:

providing an endovascular stent-graft, which is configured to assume a radially-compressed delivery state and a radially-expanded deployment state, and which includes (a) a flexible stent member, and (b) a tubular fluid flow guide, which includes a graft material, and which is attached to the stent member, wherein the stent member includes a generally circumferential section that is shaped so as to define at least one fixation member having a sharp tip;

transvascularly introducing the stent-graft into a blood vessel of a human subject while the stent-graft is in the radially-compressed delivery state, in which at least a portion of the fixation member is convex as viewed from outside the stent-graft, such that the sharp tip points radially inward; and thereafter, transitioning the stent-graft to the radially-expanded deployment state in the blood vessel, such that the fixation member protrudes radially outwardly.

For some applications, providing the stent-graft includes providing the stent-graft in which the circumferential section is at least partially not covered by the fluid flow guide at least when the stent-graft is in the radially-expanded deployment state.

For some applications, providing the stent-graft includes providing the stent-graft in which (a) the stent member is shaped so as to define a generally circumferential band, which includes the circumferential section, which is shaped so as to define at least one first strut and at least one second strut, which are coupled at a peak of the circumferential band, and (b) the fixation member is shaped so as to define a base at a first end thereof and the sharp tip at a second end thereof, which base is coupled to the first strut.

The present invention will be more fully understood from the following detailed description of applications thereof, taken together with the drawings, in which:

BRIEF DESCRIPTION OF THE DRAWINGS

FIGS. 2A-C are schematic illustrations of an endovascular stent-graft during several stages of loading the stent-graft into an external delivery sheath of a delivery catheter, in accordance with an application of the present invention;

FIGS. 3A-C are schematic illustrations of the stent-graft of FIGS. 2A-C during several stages of deployment of the stent-graft from the external delivery sheath, in accordance with an application of the present invention;

FIGS. 6A-C are schematic illustrations of another configuration the stent-graft of FIGS. 2A-C and 3A-C during several stages of deployment of the stent-graft from the external delivery sheath, in accordance with an application of the present invention;

DETAILED DESCRIPTION OF APPLICATIONS

Figure 1:
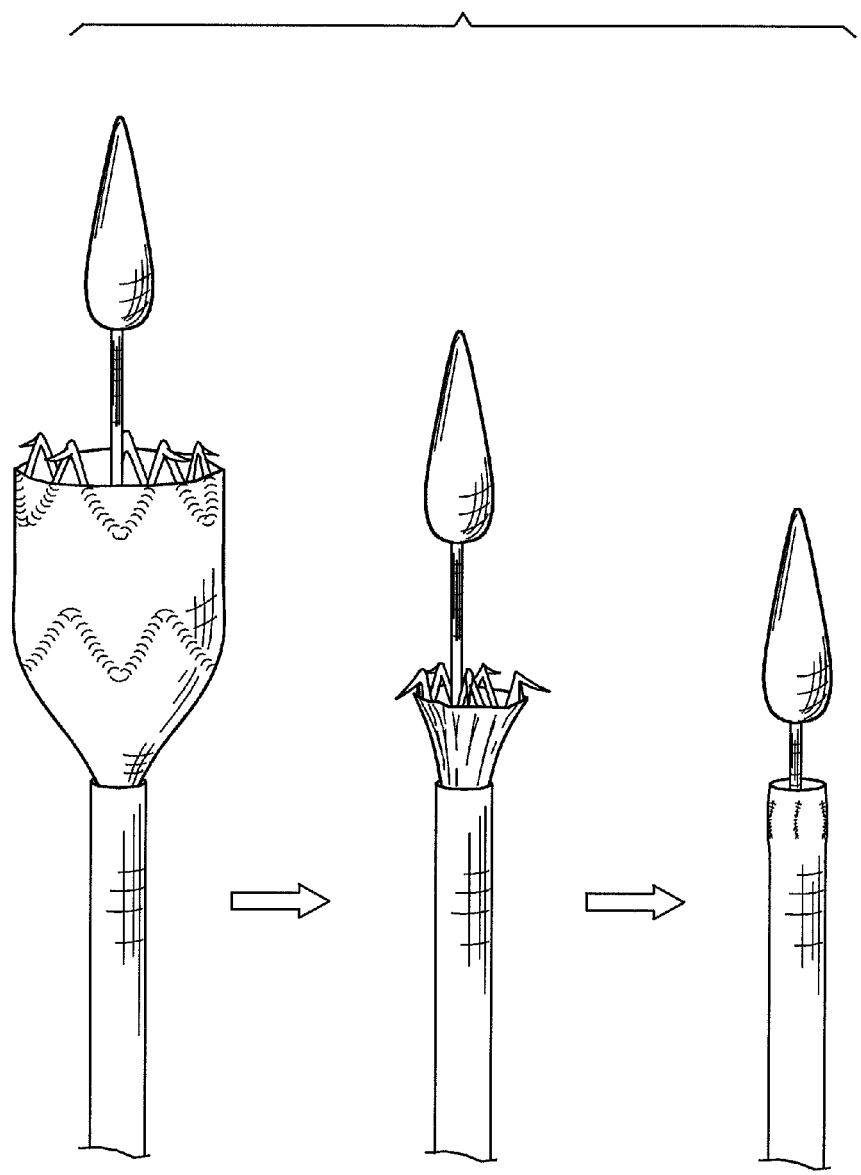
FIG. 1 is a schematic illustration of an endovascular stent-graft during several stages of loading the stent-graft into an external delivery sheath of a delivery catheter, in accordance with the prior art.

Reference is made to FIGS. 2A-C and 3A-C. FIGS. 2A-C are schematic illustrations of an endovascular stent-graft 10 during several stages of loading the stent-graft into an external delivery sheath 20 of a delivery catheter of a delivery system, in accordance with an application of the present invention. FIGS. 3A-C are schematic illustrations of stent-graft 10 during several stages of deployment of the stent-graft from external delivery sheath 20, in accordance with an application of the present invention.

Stent-graft 10 comprises a flexible stent member 24 and a tubular fluid flow guide 26. Stent-graft 10 is configured to assume (a) a radially-compressed delivery state, typically when the body is positioned in sheath 20, such as shown in FIGS. 2C and 3A, and (b) a radially-expanded deployment state, when not positioned in the sheath. FIGS. 2A and 3C show a distal portion of the body in the radially-expanded state. FIGS. 2B and 3B show a distal portion of the body partially radially expanded. FIGS. 2A-C and 3A-C also show a distal tip 30 and an inner shaft 32 of the delivery system.

Typically, external delivery sheath 20 comprises a polymer. For some applications, external delivery sheath 20 comprises an extruded polymer tube, encapsulating a metallic (or other type of very resilient polymer wire, such as Kevlar™) wire helical coil, and/or braid, which provide kink resistance, and/or longitudinal straight wires for prevention of elongation of the sheath. Optionally, an internal low-friction layer, e.g., comprising PTFE, is provided as an inner lining of the external sheath, in order to reduce frictional forces between the stent-graft and the external delivery sheath.

Fluid flow guide 26 is attached to stent member 24, such as by suturing or stitching. The flexible stent member may be attached to an internal and/or an external surface of the fluid flow guide. Flexible stent member 24 comprises a plurality of structural stent elements 28, which are either indirectly connected to one another by the fluid flow guide (as shown), or interconnected with one another (configuration not shown). Optionally, a portion of the structural stent elements may be attached (e.g., sutured) to the internal surface of the fluid flow guide, and another portion to the external surface of the fluid flow guide. For some applications, structural stent elements 24 comprise a metal. Alternatively or additionally, the structural stent elements comprise a self-expanding material, such that stent-graft 10 is self-expandable. Alternatively or additionally, the structural stent elements comprise one or more metallic alloys, such as one or more superelastic metal alloys, a shape memory metallic alloy, and/or Nitinol. For some applications, the stent-graft is heat-set to assume the radially-expanded state.

Fluid flow guide 26 comprises a graft material, i.e., at least one biologically-compatible substantially blood-impervious flexible sheet. The flexible sheet may comprise, for example, a polyester, a polyethylene (e.g., a poly-ethylene-terephthalate), a polymeric film material (e.g., polytetrafluoroethylene), a polymeric textile material (e.g., woven polyethylene terephthalate (PET)), natural tissue graft (e.g., saphenous vein or collagen), Polytetrafluoroethylene (PTFE), ePTFE, Dacron, or a combination of two or more of these materials. The graft material optionally is woven.

Typically, stent-graft 10 is configured to self-expand from the delivery state to the deployment state, such as shown in FIGS. 3A-C. (FIG. 3C shows a distal portion of the stent-graft radially expanded in the deployment state; the remainder of the stent-graft transitions to the deployment state when external delivery sheath 20 is subsequently fully withdrawn from the stent-graft.) For example, stent member 24 may be heat-set to cause stent-graft 10 to self-expand from the delivery state to the deployment state.

Fluid flow guide 26 is attached to stent member 24 such that at least a generally circumferential section 40 of the stent member is at least partially, e.g., completely, not covered by the fluid flow guide at least when the stent-graft is in the radially-expanded deployment state. Typically, the circumferential section is disposed at an end of stent-graft 10, such as a distal end of the stent-graft as shown in FIGS. 2A-C and 3A-C.

For some applications, circumferential section 40 is shaped so as to define a plurality of first struts 42 and a plurality of second struts 43. Circumferential section 40 is shaped so as to further define a plurality of fixation members 44, which are coupled to respective ones of first struts 42. (The fixation members may be "coupled" to the struts by fabricating the fixation members and struts from a single piece, e.g., from a rectangular blank by removing missing portions by any standard means such as punching, stamping, milling, or laser cutting; alternatively, the fixation members may comprises separate pieces, which are fixed to the struts during fabrication.) For some applications, one or more (e.g., all) of fixation members 44 are shaped so as to define respective barbs, typically including sharp tips 45 for penetrating tissue, e.g., of an inner wall of a blood vessel. As used in the present application, including in the claims, a "barb" means an element having at least one free sharp end, which is sharp enough to enter the aortic wall. The element may or may not define a sharp projection extending backward from the sharp end for preventing easy extraction. Fixation members 44 are shown as narrowing toward tips 45 in FIGS. 2A-C and 3A-C (and FIGS. 4A-C, 5A-B, and 6A-C, described hereinbelow). Alternatively, the width of the fixation members remains generally constant along at least a portion of, e.g., all of, the length thereof, e.g., similar to the configuration shown in FIGS. 8A-B.

For some applications, as shown in FIGS. 2A-B and 3B-C (and FIGS. 4A-C, 5A-B, and 6A-C, described hereinbelow) circumferential section 40 is configured such that:

when stent-graft 10 is in the delivery state, second struts 43 radially constrain fixation members 44, respectively, including sharp tips 45, respectively, from protruding radially outward, and when stent-graft 10 is in the deployment state, fixation members 44 are not radially-constrained by second struts 43 and protrude radially outward. In this state, tips 45 of fixation members 44 typically extend in respective directions that define angles of between 40 and 90 degrees with an external surface of stent-graft 10. Typically, fixation member 44 are heat-set to protrude radially outward when not confined by second struts 43.

When the stent-graft is in the delivery state, radially-constrained fixation members 44 are unlikely to penetrate, tear, or otherwise damage external delivery sheath 20. When the stent-graft is in the deployment state, fixation members 44 are configured to penetrate the inner wall of a tubular body part, such as a blood vessel, in order to help anchor stent-graft 10 to the blood vessel.

As mentioned above, when stent-graft 10 is in the delivery state, second struts 43 radially constrain respective fixation members 44 from protruding radially outward. Typically, second struts 43 are closer to first struts 42 when stent-graft 10 is in the delivery state (and the stent-graft is thus radially compressed and consequently also circumferentially compressed) than when stent-graft 10 is in the deployment state. As a result, for some applications, second struts 43 are close enough to first struts 42 to come in contact with respective portions of fixation members 44 and block the fixation members from protruding radially outward. Fixation members 44 are disposed radially inward of second struts 43, resting against respective surfaces of second struts 43 that face radially inward, such as shown in FIGS. 2B, 3B, 4B-C, and 6B. In contrast, when stent-graft 10 is in the deployment state, second struts 43 are too far from first struts 42 to come in contact with respective fixation members 44, which are thus free to expand radially outward, such as shown in FIGS. 2A, 3C, 4A, and 6C.

In some applications of the present invention, a method is provided for loading stent-graft 10 into external delivery sheath 20. Stent-graft 10 is provided in the radially-expanded deployment state, and loaded into external delivery sheath 20, such that the stent-graft assumes the radially-compressed delivery state, in which second struts 43 radially constrain fixation members 44, respectively, from protruding radially outward. Typically, fixation members 44 are loaded into the external delivery sheath after the second struts and fixation members have been positioned such that the second struts radially constrain the fixation members, as shown in FIG. 2B. For some applications, a jig (not shown) may be used to push fixation members 44 radially inward and optionally also laterally, during the crimping and constraining process. The stent-graft may be held in a partially radially-compressed state at this point in the loading procedure, as shown in FIG. 2B.

For some applications, such as shown in FIGS. 2A-B and 3B-C (and FIGS. 4A-C, 5A-B, and 6A-C, described hereinbelow), stent member 24 is shaped so as to define a generally circumferential band 50, which includes circumferential section 40 and first and second struts 42 and 43. Circumferential band 50 is shaped such that pairs 52 of first and second struts 42 and 43 are coupled at respective peaks 54 of circumferential band 50. As used in the present application, including the claims, a "pair" consists of exactly two elements; each pair 52 consists of exactly one of first struts 42 and exactly one of second struts 43. Typically, fixation members 44 are shaped so as to define respective bases 60 at respective first ends thereof and respective sharp tips 45 at respective second ends thereof. Bases 60 are coupled to respective ones of first struts 42. For some applications, bases 60 are coupled to respective first struts 42 within a distance of the respective peaks, which distance equals 50% of a length of first struts 42. For some applications, peaks 54 are curved.

Figure 4A:
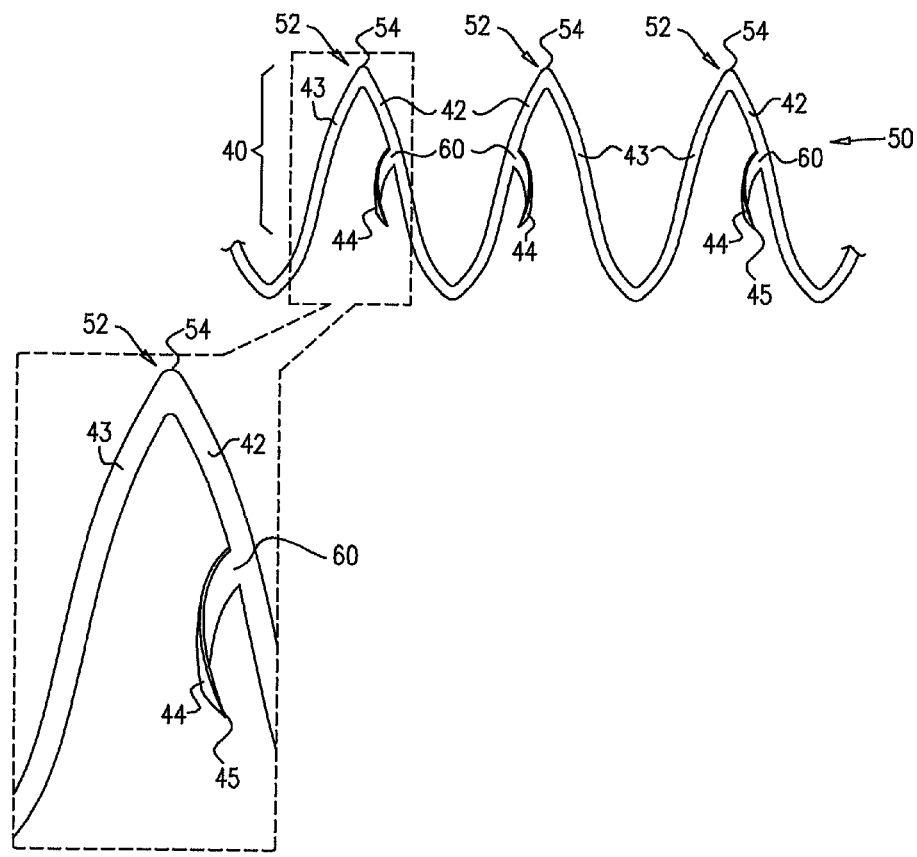
FIGS. 4A-C are schematic illustrations of a portion of a circumferential band of the stent-graft of FIGS. 2A-C and 3A-C in several states, respectively, in accordance with an application of the present invention.
Figure 4B:
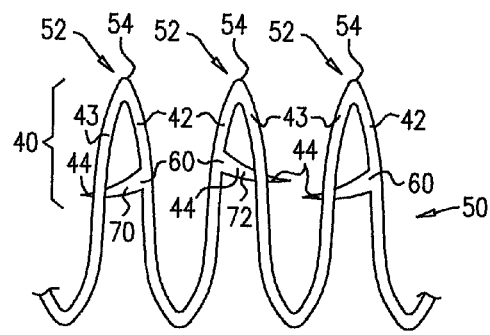
Figure 4C:
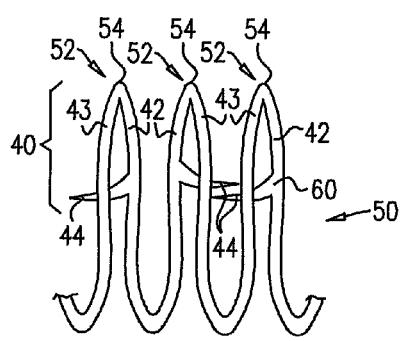

Reference is now made to FIGS. 4A-C, which are schematic illustrations of a portion of circumferential band 50 in several states, respectively, in accordance with an application of the present invention. FIGS. 4A-C show the portion of circumferential band 50 viewed from outside the stent-graft. FIG. 4A shows circumferential band 50 when the stent-graft is in the deployment state, in which fixation members 44 are not radially-constrained by respective second struts 43 and protrude radially outward. FIGS. 4B and 4C show stent-graft 10 at two levels of radial compression. One of these levels of compression, or an intermediary level of compression, may occur in the delivery state, depending on the inner diameter of external delivery sheath 20 and the crossing profile of the stent-graft. At these levels of compression, one or more second struts 43 of circumferential section 40 radially constrain respective fixation members 44 from protruding radially outward.

Figure 5A:
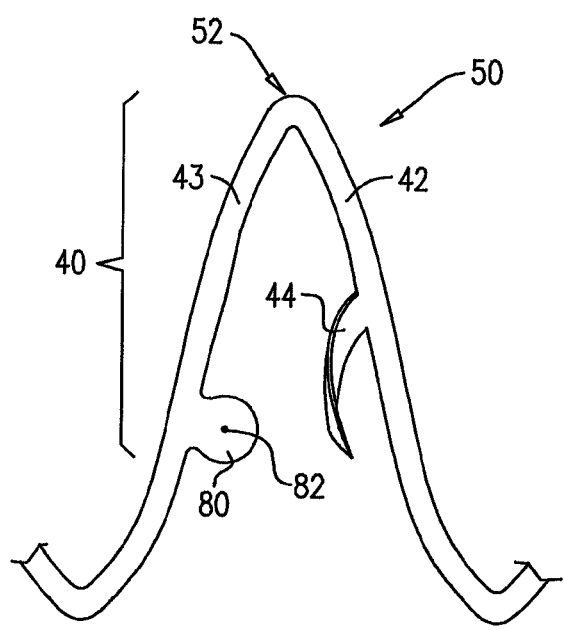
FIGS. 5A-B are schematic illustrations of a portion of the circumferential band of FIGS. 2A-C and 3A-C in two states, respectively, in accordance with an application of the present invention.
Figure 5B:
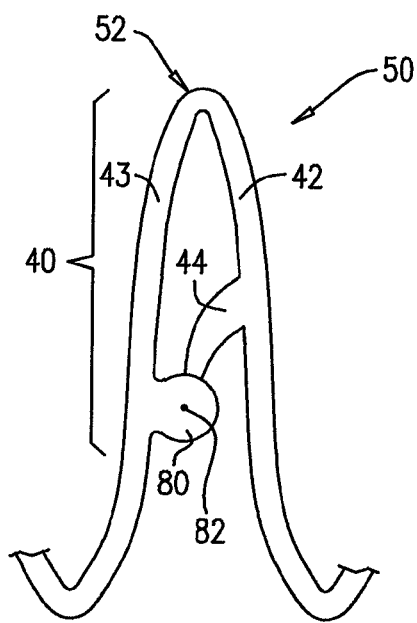

Reference is now made to FIGS. 5A-B, which are schematic illustrations of a portion of circumferential band 50 in two states, respectively, in accordance with an application of the present invention. FIGS. 5A-B show the portion of circumferential band 50 viewed from outside the stent-graft. FIG. 5A shows circumferential band 50 when the stent-graft is in the deployment state, in which fixation members 44 are not radially-constrained by respective second struts 43 and protrude radially outward. FIG. 5B shows circumferential band 50 when second struts 43 radially constrain respective fixation members 44 from protruding radially outward constrained by respective and protrude radially outward, such as when the stent-graft is in the deployment state. In this configuration, second struts 43 are shaped so as to define respective lateral protrusions 80. Lateral protrusions 80 constrain respective ones of tips 45 from protruding radially outward, and thus possibly damaging the inner surface of the external delivery sheath, when the stent-graft is in the radially-compressed delivery state, such that second struts 43 constrain the respective tips from protruding radially outward when the stent-graft is in the radially-compressed delivery state.

Typically, second struts 43 are closer to first struts 42 when stent-graft 10 is in the delivery state than when stent-graft 10 is in the deployment state. As a result, for some applications, second struts 43 are close enough to first struts 42 for lateral protrusions to come in contact with respective portions of fixation members 44 and block the fixation members from protruding radially outward. Fixation members 44 are disposed radially inward of second struts 43, resting against respective surfaces of lateral protrusions 80 that face radially inward, as shown in FIG. 5B. In contrast, when stent-graft 10 is in the deployment state, second struts 43 are too far from first struts 42 for lateral protrusions 80 to come in contact with respective fixation members 44, which are thus free to expand radially outward, such as shown in FIG. 5A.

For some applications, one or more of lateral protrusions 80 comprise respective radiopaque markers 82, which may aid in properly positioning and/or rotationally aligning the stent-graft during deployment and/or implantation.

Reference is again made to FIGS. 2A-C, 3A-C, 4A-C, and 5A-B, as well as to FIGS. 6A-C, which are schematic illustrations of another configuration stent-graft 10 during several stages of deployment of the stent-graft from external delivery sheath 20, in accordance with an application of the present invention. In the configurations shown in FIGS. 2A-C, 3A-C, 4A-C, and 5A-B, fixations members 44 are radially outwardly curved when in the deployment state. Alternatively, in the configuration shown in FIGS. 6A-C, fixation members 44 are flat when in the deployment state. In this configuration, fixation members 44 typically articulate with respect to respective first struts 42 at the respective bases 60 of the fixation members, at the sites of coupling with first struts 42. This flat configuration may be implemented with any of the configurations described herein, including with reference to FIGS. 4A-C and FIGS. 5A-B.

Figure 7:
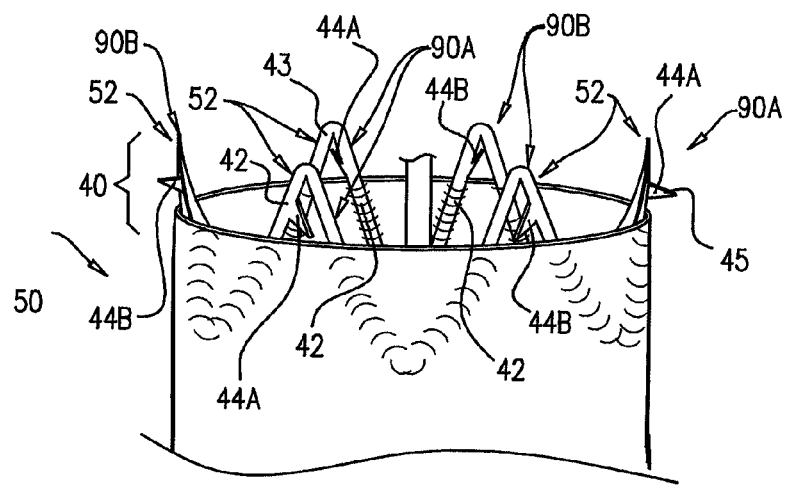
FIG. 7 is a schematic illustration of a portion of the stent-graft of FIGS. 2A-C and 3A-C, in accordance with an application of the present invention.

Reference is again made to FIGS. 2A-C, 3A-C, 4A-C, 5A-B, and 6A-C, as well as to FIG. 7, which is a schematic illustration of a portion of stent-graft 10, in accordance with an application of the present invention. For some applications, such as shown in these figures, a first subset of fixation members 44 (labeled 44A) extend in a counterclockwise direction (e.g., as viewed from a distal end of the stent-graft, i.e., from above in FIG. 7) from their respective first struts 42, and a second subset of fixation members 44 (labeled 44B) extend in a clockwise direction (e.g., as viewed from a distal end of the stent-graft, i.e., from above in FIG. 7) from their respective first struts 42. (When the stent-graft is in the deployment state, the direction of the fixation members also includes a radially-outward component, i.e., the fixation members protrude radially outward.) Thus, a first subset 90A of pairs 52 of struts are configured such that first struts 42 thereof are disposed clockwise (e.g., as viewed from a distal end of the stent-graft) with respect to second struts 43 thereof, and a second subset 90B of pairs 52 of struts are configured such that first struts 42 thereof are disposed counterclockwise (e.g., as viewed from a distal end of the stent-graft) with respect to second struts 43 thereof.

For some applications, fixation members 44A and 44B are arranged alternatingly around circumferential section 40, i.e., fixation member 44A, fixation member 44B, fixation member 44A, fixation member 44B, etc. For these applications, pairs 52 of struts 42 and 43 of first subset 90A and pairs 52 of struts 42 and 43 of second subset 90B are arranged alternatingly around circumferential section 40.

This arrangement of the fixation members may help better anchor stent-graft 10 to the wall of the blood vessel. For example, blood flow in tortuous blood vessels may cause some rotation of the blood vessel. Because some fixation members 44 point in each direction (clockwise and counterclockwise), a subset of the fixation members anchors better regardless of the direction in which the blood vessel rotates (clockwise or counterclockwise).

Figure 8A:
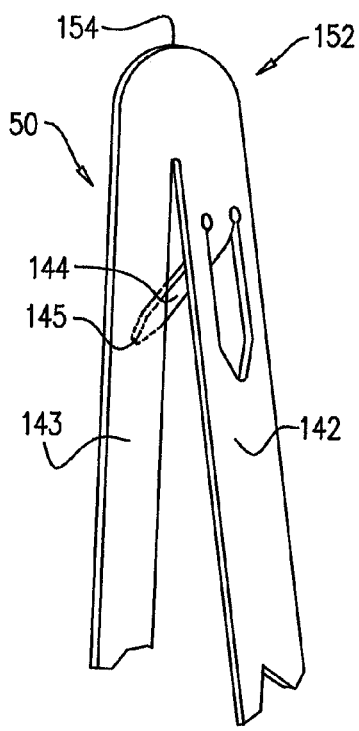
FIGS. 8A-B are schematic illustrations of another configuration of a portion of a circumferential band of the stent-graft 2A-C and 3A-C in several states, respectively, in accordance with an application of the present invention.
Figure 8B:
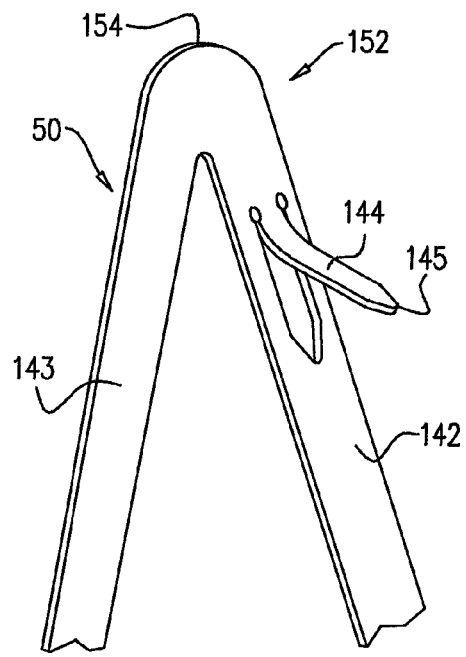

Reference is now made to FIGS. 8A-B, which are schematic illustrations of another configuration of a portion of circumferential band 50 in two respective states, in accordance with an application of the present invention. FIGS. 8A-B show the portion of circumferential band 50 viewed from outside the stent-graft. This configuration may be used in combination with the configurations described hereinabove with reference to FIGS. 1A-C, 2A-C, and/or 6A-C. In this configuration, circumferential band 50 is shaped such that pairs 152 of first and second struts 142 and 143 are coupled at respective peaks 154 of circumferential band 50. Fixation members 144 are coupled to respective ones of first struts 142.

FIG. 8A shows circumferential band 50 when stent-graft 10 is in the delivery state, in which second strut 143 radially constrains fixation member 144 from protruding radially outward. FIG. 8B shows circumferential band 50 when the stent-graft is in the deployment state, in which fixation members 144 are not radially-constrained by respective second struts 143 and protrude radially outward.

In this configuration, fixation member 144 is shaped as a tab that is cut from first strut 142 on all sides of the tab except at a base 160 thereof that is coupled to first strut 142. For example, the tab may be manufactured by making a U- or V-shaped cut in first strut 142. Fixation member 144 may be generally flat, as shown in FIGS. 8A-B, or curved when in the deployment state (configuration not shown). Typically, fixation member 144 is heat-set to assume the state shown in FIG. 8B. If the tab is straightened such that a surface thereof is parallel with a surface of first strut 142, the tab is surrounded on all sides thereof by first strut 142.

Typically, second struts 143 are closer to first struts 142 when the stent-graft is in the delivery state than when the stent-graft is in the deployment state. As a result, for some applications, second struts 143 are close enough to first struts 142 to come in contact with respective portions of fixation members 144 and block the fixation members from protruding radially outward. Fixation members 144 are disposed radially inward of second struts 143, resting against respective surfaces of second struts 143 that face radially inward, such as shown in FIG. 8A. In contrast, when the stent-graft is in the deployment state, second struts 143 are too far from first struts 142 to come in contact with respective fixation members 144, which are thus free to expand radially outward, such as shown in FIG. 8B.

Figure 9A:
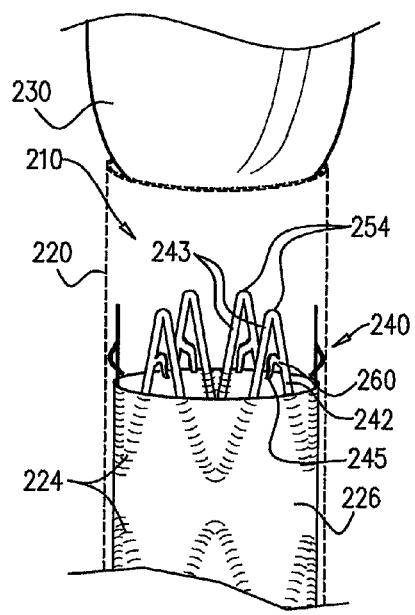
FIGS. 9A-B are schematic illustrations of another stent-graft during two stages of deployment of the stent-graft from an external delivery sheath of a delivery catheter, in accordance with an application of the present invention.
Figure 9B:
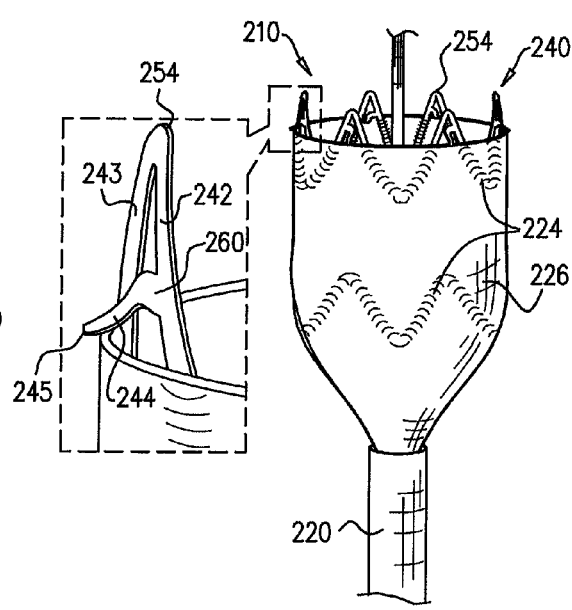

Reference is now made to FIGS. 9A-B, which are schematic illustrations of a stent-graft 210 during two stages of deployment of the stent-graft from a external delivery sheath 220, in accordance with an application of the present invention. FIGS. 9A and 9B are shown in different scales, with greater enlargement of the device in FIG. 9A than in FIG. 9B; sheath 220 is in practice exactly or approximately the same size in FIGS. 9A and 9B. Stent-graft 210 comprises a flexible stent member 224 and a tubular fluid flow guide 226. Stent-graft 210 is configured to assume (a) a radially-compressed delivery state, typically when the body is positioned in sheath 220, such as shown in FIG. 9A, and (b) a radially-expanded deployment state, when not positioned in the sheath. FIG. 9B shows a distal portion of the body in the radially-expanded state. FIG. 9A also shows a distal tip 230 and an inner shaft 232 of the delivery system.

Fluid flow guide 226 is attached to stent member 224, such as described hereinabove with reference to FIGS. 2A-C and 3A-C regarding fluid flow guide 26 and stent member 24. Fluid flow guide 226 comprises a graft material, such as described hereinabove with reference to FIGS. 2A-C and 3A-C regarding fluid flow guide 26. Typically, stent-graft 210 is configured to self-expand from the delivery state to the deployment state, such as shown in FIGS. 9A-B. (FIG. 9B shows a distal portion of the stent-graft radially expanded in the deployment state; the remainder of the stent-graft transitions to the deployment state when external delivery sheath 220 is subsequently fully withdrawn from the stent-graft.) For example, stent member 224 may be heat-set to cause stent-graft 210 to self-expand from the delivery state to the deployment state.

Fluid flow guide 226 is attached to stent member 224 such that at least a generally circumferential section 240 of the stent member is at least partially, e.g., completely, not covered by the fluid flow guide at least when the stent-graft is in the radially-expanded deployment state. Typically, the circumferential section is disposed at an end of stent-graft 210, such as a distal end of the stent-graft as shown in FIGS. 9A-B.

Circumferential section 240 is shaped so as to define a plurality of first struts 242 and a plurality of second struts 243. Circumferential section 240 is shaped so as to further define a plurality of fixation members 244, which are coupled to respective ones of first struts 242. (The fixation members may be "coupled" to the struts by fabricating the fixation members and struts from a single piece, e.g., from a rectangular blank by removing missing portions by any standard means such as punching, stamping, milling, or laser cutting; alternatively, the fixation members may comprises separate pieces, which are fixed to the struts during fabrication.) For some applications, one or more (e.g., all) of fixation members 244 are shaped so as to define respective barbs, typically including sharp tips 245 for penetrating tissue, e.g., of an inner wall of a blood vessel. As used in the present application, including in the claims, a "barb" means an element having at least one free sharp end, which is sharp enough to enter the aortic wall. The element may or may not define a sharp projection extending backward from the sharp end for preventing easy extraction.

Figure 10A:
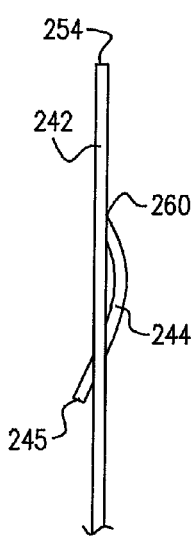
FIGS. 10A-C are schematic side views of a single one of the fixation members and a single one of the first struts of the stent-graft of FIGS. 9A-B, in several deployment states, in accordance with an application of the present invention.
Figure 10B:
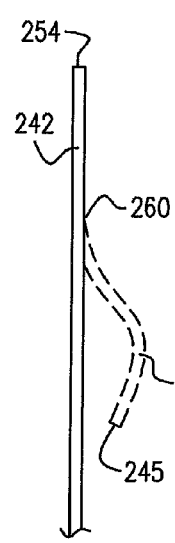
Figure 10C:
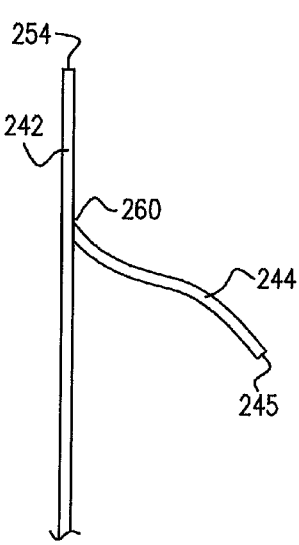

Reference is still made to FIGS. 9A-B, and is additionally made to FIGS. 10A-C, which are schematic side views of a single one of fixation members 244 and a single one of first struts 242, in several deployment states, in accordance with an application of the present invention. Each of these figures shows a single one of first struts 242 and a single one of fixation members 244 coupled thereto in side view, in which the radially-outward direction is the rightward direction in FIGS. 10A-C (second struts are directly behind first struts 242, and thus cannot be seen in the figures).

Fixation member 244 is shaped so as to define a base 260 at a first end thereof and sharp tip 245 at a second end thereof. Base 260 is coupled to first strut 242. For some applications, base 260 is coupled to first strut 242 within a distance of a peak 254 of the pair including the first and second struts, which distance equals 50% of a length of the first strut. For some applications, peak 254 is curved.

FIGS. 9A and 10A show first strut 242 and fixation member 244 when stent-graft 210 is in the radially-compressed delivery state. In this state, at least a portion of fixation member 244 is convex as viewed from outside stent-graft 210, such that sharp tip 245 points radially inward (i.e., to the left in FIG. 10A, toward a central longitudinal axis of stent-graft 210). Fixation member 244 is bent radially inward. Typically, tip 245 is positioned more radially inward than is first strut 242.

When stent-graft 210 is in the radially-expanded deployment state, as shown in FIGS. 9B and 10C, fixation member 244 and sharp tip 245 protrude radially outward (i.e., to the right in FIG. 10C, away from a central longitudinal axis of stent-graft 210), typically beyond all other portions of fixation member 244 and first strut 242.

When the stent-graft is in the delivery state, radially-constrained fixation members 44 are unlikely to penetrate, tear, or otherwise damage external delivery sheath 220. When the stent-graft is in the deployment state, fixation members 244 are configured to penetrate the inner wall of a tubular body part, such as a blood vessel, in order to help anchor stent-graft 210 to the blood vessel.

Reference is made to FIGS. 2A-10C. For some applications, during a first stage of an implantation procedure, the stent-graft is transvascularly (typically percutaneously) introduced into a blood vessel of a human subject, such as an aorta, while the stent-graft is positioned in external delivery sheath 20 in the radially-compressed delivery state. The external delivery sheath is advanced to a desired deployment location in the blood vessel, such at or slightly above the renal arteries. The external delivery sheath is proximally withdrawn, releasing the stent-graft in the aorta. As the stent-graft is released, the stent-graft transitions to the radially-expanded deployment state in the blood vessel. In this state, the fixation members protrude radially outward and enter tissue of the internal wall of the blood vessel, helping to anchor the stent-graft in place.

Optionally, after the stent-graft has radially expanded, the surgeon rotates the stent-graft slightly, in order to better engage the fixation members with the tissue of the vessel wall. Alternatively or additionally, for some applications, a balloon is used to radially expand the stent-graft, and the balloon is configured to inflate with a rotational vector.

As used in the present application, including in the claims, "tubular" means having the form of an elongated hollow object that defines a conduit therethrough. A "tubular" structure may have varied cross-sections therealong, and the cross-sections are not necessarily circular. For example, one or more of the cross-sections may be generally circular, or generally elliptical but not circular, or circular.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

PCT Application PCT/IL2008/000287, filed Mar. 5, 2008, which published as PCT Publication WO 2008/107885 to Shalev et al., and U.S. application Ser. No. 12/529,936 in the national stage thereof, which published as US Patent Application Publication 2010/0063575 to Shalev et al.

U.S. Provisional Application 60/892,885, filed Mar. 5, 2007

PCT Application PCT/IL2007/001312, filed Oct. 29, 2007, which published as PCT Publication WO/2008/053469 to Shalev, and U.S. application Ser. No. 12/447,684 in the national stage thereof, which published as US Patent Application Publication 2010/0070019 to Shalev U.S. Provisional Application 60/991,726, filed Dec. 2, 2007

PCT Application PCT/IL2008/001621, filed Dec. 15, 2008, which published as PCT Publication WO 2009/078010, and U.S. application Ser. No. 12/808,037 in the national stage thereof, which published as US Patent Application Publication 2010/0292774

U.S. Provisional Application 61/219,758, filed Jun. 23, 2009

U.S. Provisional Application 61/221,074, filed Jun. 28, 2009

PCT Application PCT/IB2010/052861, filed Jun. 23, 2010, which published as PCT Publication WO 2010/150208, and U.S. application Ser. No. 13/380,278 in the national stage thereof, now U.S. Pat. No. 8,870,938

PCT Application PCT/IL2010/000549, filed Jul. 8, 2010, which published as PCT Publication WO 2011/004374

PCT Application PCT/IL2010/000564, filed Jul. 14, 2010, which published as PCT Publication WO 2011/007354, and U.S. application Ser. No. 13/384,075 in the national stage thereof, which published as US Patent Application Publication 2012/0179236

PCT Application PCT/IL2010/000917, filed Nov. 4, 2010, which published as PCT Publication WO 2011/055364

PCT Application PCT/IL2010/000999, filed Nov. 30, 2010, which published as PCT Publication WO 2011/064782

PCT Application PCT/IL2010/001018, filed Dec. 2, 2010, which published as PCT Publication WO 2011/067764

PCT Application PCT/IL2010/001037, filed Dec. 8, 2010, which published as PCT Publication WO 2011/070576

PCT Application PCT/IL2010/001087, filed Dec. 27, 2010, which published as PCT Publication WO 2011/080738

PCT Application PCT/IL2011/000135, filed Feb. 8, 2011, which published as PCT Publication WO 2011/095979

PCT Application PCT/IL2011/000801, filed Oct. 10, 2011, which published as PCT Publication WO 2012/049679

U.S. application Ser. No. 13/031,871, filed Feb. 22, 2011, which published as US Patent Application Publication 2011/0208289

U.S. Provisional Application 61/496,613, filed Jun. 14, 2011

U.S. Provisional Application 61/505,132, filed Jul. 7, 2011

U.S. Provisional Application 61/529,931, filed Sep. 1, 2011

U.S. Provisional Application 61/529,931, filed Sep. 1, 2011

PCT Application PCT/IL2012/000148, filed Apr. 4, 2012, which published as PCT Publication WO 2013/030818

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising an endovascular stent-graft, which is configured to assume a radially-compressed delivery state and a radially-expanded deployment state, and which comprises:
    a flexible stent member, which comprises a plurality of struts, which are shaped so as to define a generally circumferential section;
    a tubular fluid flow guide, which comprises a graft material, and which is attached to the stent member; and
    at least one fixation member shaped so as to define a base at a first end thereof and a sharp tip at a second end thereof, wherein the base is coupled to one of the struts that are shaped so as to define the generally circumferential section,
    wherein, when the stent-graft is in the radially-expanded deployment state, the fixation member protrudes radially outward, and
    wherein, when the stent-graft is in the radially-compressed delivery state, at least a portion of the fixation member between the base and the sharp tip is convex as viewed from outside the stent-graft, such that the sharp tip points radially inward.

2. The apparatus according to claim 1,
    wherein the stent member is shaped so as to define a generally circumferential band, which includes the circumferential section, and
    wherein the plurality of struts that are shaped so as to define the generally circumferential section include (a) the one of the struts to which the base is coupled and (b) a second strut, which are coupled at a peak of the circumferential band.

3. The apparatus according to claim 1, wherein the circumferential section is at least partially not covered by the fluid flow guide at least when the stent-graft is in the radially-expanded deployment state.

4. The apparatus according to claim 1,
wherein, when the stent-graft is in the radially-compressed delivery state, the sharp tip is positioned more radially inward than is the one of the struts to which the base is coupled.

5. The apparatus according to claim 1, wherein, when the stent-graft is in the radially-expanded deployment state, a portion of the fixation member between the base and the sharp tip is convex as viewed from outside the stent-graft.

6. A method comprising:
providing an endovascular stent-graft in a radially-expanded deployment state, which stent-graft includes (a) a flexible stent member, which includes a plurality of struts, which are shaped so as to define a generally circumferential section, (b) a tubular fluid flow guide, which includes a graft material, and which is attached to the stent member, and (c) at least one fixation member shaped so as to define a base at a first end thereof and a sharp tip at a second end thereof, wherein the base is coupled to one of the struts that are shaped so as to define the generally circumferential section, and wherein, when the stent-graft is in the deployment state, the fixation members protrudes radially outward; and
loading the stent-graft into an external delivery sheath of a delivery catheter, such that the stent-graft assumes a radially-compressed delivery state, in which at least a portion of the fixation member between the base and the sharp tip is convex as viewed from outside the stent-graft, such that the sharp tip points radially inward.

7. The method according to claim 6, wherein providing the stent-graft comprises providing the stent-graft in which the circumferential section is at least partially not covered by the fluid flow guide at least when the stent-graft is in the radially-expanded deployment state.

8. The method according to claim 6,
wherein providing the stent-graft comprises providing the stent-graft in which the stent member is shaped so as to define a generally circumferential band, which includes the circumferential section, and
wherein the plurality of struts that are shaped so as to define the generally circumferential section include (a) the one of struts to which the base is coupled and (b) a second strut, which are coupled at a peak of the circumferential band.

9. The method according to claim 6,
wherein loading comprises loading the stent-graft into the external delivery sheath such that the stent-graft assume the radially-compressed delivery state, in which the sharp tip is positioned more radially inward than is the one of the struts to which the base is coupled.

10. The method according to claim 6, wherein providing the stent-graft comprises providing the stent-graft in the radially-expanded deployment state in which a portion of the fixation member between the base and the sharp tip is convex as viewed from outside the stent-graft.

11. A method comprising:
providing an endovascular stent-graft, which is configured to assume a radially-compressed delivery state and a radially-expanded deployment state, and which includes (a) a flexible stent member, which includes a plurality of struts, which are shaped so as to define a generally circumferential section, (b) a tubular fluid flow guide, which includes a graft material, and which is attached to the stent member, and (c) at least one fixation member shaped so as to define a base at a first end thereof and a sharp tip at a second end thereof, wherein the base is coupled to one of the struts that are shaped so as to define the generally circumferential section;
transvascularly introducing the stent-graft into a blood vessel of a human subject while the stent-graft is in the radially-compressed delivery state, in which at least a portion of the fixation member between the base and the sharp tip is convex as viewed from outside the stent-graft, such that the sharp tip points radially inward; and
thereafter, transitioning the stent-graft to the radially-expanded deployment state in the blood vessel, such that the fixation member protrudes radially outwardly.

12. The method according to claim 11, wherein providing the stent-graft comprises providing the stent-graft in which the circumferential section is at least partially not covered by the fluid flow guide at least when the stent-graft is in the radially-expanded deployment state.

13. The method according to claim 11, wherein providing the stent-graft comprises providing the stent-graft in which (a) the stent member is shaped so as to define a generally circumferential band, which includes the circumferential section, and (b) the plurality of struts that are shaped so as to define the generally circumferential section include (i) the one of the struts to which the base is coupled and (ii) a second strut, which are coupled at a peak of the circumferential band.

14. The method according to claim 11,
wherein transvascularly introducing the stent-graft comprises transvascularly introducing the stent-graft into the blood vessel while the stent-graft is in the radially-compressed delivery state, in which the sharp tip is positioned more radially inward than is the one of the struts to which the base is coupled.

15. The method according to claim 11, wherein transitioning comprises transitioning the stent-graft to the radially-expanded deployment state in the blood vessel, such that a portion of the fixation member between the base and the sharp tip is convex as viewed from outside the stent-graft.

* * * * *